(12) United States Patent
Milburn et al.

(10) Patent No.: US 9,109,252 B2
(45) Date of Patent: Aug. 18, 2015

(54) IDENTITY ELUCIDATION OF UNKNOWN METABOLITES

(75) Inventors: Michael Milburn, Cary, NC (US); Gabriele Kastenmueller, Grafing (DE); Jan Krumsiek, Munich (DE); Karsten Suhre, Doha (QA)

(73) Assignees: Metabolon, Inc., Durham, NC (US); Helmholtz Zentrum Munchen, Neuherberg (DE)

( * ) Notice: Subject to any disclaimer, the term of this patent is extended or adjusted under 35 U.S.C. 154(b) by 0 days.

(21) Appl. No.: 14/128,107

(22) PCT Filed: Jun. 21, 2012

(86) PCT No.: PCT/US2012/043461
§ 371 (c)(1),
(2), (4) Date: Mar. 19, 2014

(87) PCT Pub. No.: WO2013/006278
PCT Pub. Date: Jan. 10, 2013

(65) Prior Publication Data
US 2014/0212872 A1    Jul. 31, 2014

Related U.S. Application Data

(60) Provisional application No. 61/503,673, filed on Jul. 1, 2011.

(51) Int. Cl.
*C12Q 1/68* (2006.01)
*G01N 33/68* (2006.01)

(52) U.S. Cl.
CPC ............... *C12Q 1/6872* (2013.01); *C12Q 1/68* (2013.01); *G01N 33/6848* (2013.01); *G01N 2570/00* (2013.01); *G01N 2800/7066* (2013.01)

(58) Field of Classification Search
USPC ........................................ 435/6.11, 4; 702/23
See application file for complete search history.

(56) References Cited

U.S. PATENT DOCUMENTS

| 6,287,765 B1 * | 9/2001 | Cubicciotti ................. 435/6.11 |
| 2004/0024543 A1 * | 2/2004 | Zhang et al. .................... 702/32 |
| 2008/0161228 A1 | 7/2008 | Ryals et al. |
| 2009/0179147 A1 | 7/2009 | Milgram et al. |

OTHER PUBLICATIONS

De Carvalho, L.P., et al., "Activity-Based Metabolomic Profiling of Enzymatic Function: Identification of Rv1248c as a Mycobacterial 2-hydroxy-3-oxoadipate Synthase", *Chem. Biol.*, (Apr. 23, 2010), 17(4):323-332.
International Search Report for PCT/US2012/043461, dated Dec. 19, 2012.

* cited by examiner

*Primary Examiner* — Ralph Gitomer
(74) *Attorney, Agent, or Firm* — Brinks Gilson & Lione

(57) ABSTRACT

A method of elucidating the identity of an unknown metabolite comprising measuring amounts of known and unknown metabolites in subjects; associating the unknown metabolite with a specific gene from a gene association study; determining a protein associated with the specific gene and analyzing information for the protein; associating the unknown metabolite with concentrations and/or ratios of other metabolites in subjects; obtaining chemical structural data for the unknown metabolite; and using the information obtained to elucidate the identity of the unknown metabolite.

19 Claims, 8 Drawing Sheets

IDENTITY ELUCIDATION OF UNKNOWN METABOLITES

CROSS REFERENCE TO RELATED APPLICATIONS

This application is a National Stage application filed under Rule 371 based upon PCT/US12/43461 filed Jun. 21, 2012, which claims the benefit of U.S. Provisional Patent Application No. 61/503,673, filed Jul. 1, 2011, the entire content of which is hereby incorporated by reference.

BACKGROUND

The ability to determine the identity of a chemical entity in a complex mixture has a broad range of highly useful applications. The techniques traditionally used in analysis of complex mixtures include chromatography and mass spectrometry. Although both chromatography and mass spectrometry separate a complex mixture into constituent parts, neither technique provides direct identification of the chemical constituents. Rather, the identity of a chemical constituent must be determined based on an analysis of the measured characteristics of the chemical constituent.

As used herein, the term "identification" as applied to chemical entities refers to the high confidence determination of the identity of a chemical entity. An example of identification is the determination that a molecule having 7 carbon atoms, 7 hydrogen atoms, a nitrogen atom, and 2 oxygen atoms is anthranilic acid rather than salicylamide, both of which have the same chemical formula $C_7H_7NO_2$.

This ability to perform non-targeted analysis, such as initial detection and subsequent recognition of unknown metabolites, has enormous benefits. For example, in a metabolic analysis of cells with and without cancer, if the analysis results show that cancerous cells almost always contain a certain unknown molecule while healthy cells do not; these results give important direction to research for detection or treatment of that cancer.

Metabolomics includes the ability to perform non-targeted analysis, which means that a chemical constituent may be detected and subsequently recognized, even though it may not be identified.

Currently, methods exist to determine the elemental compositions of ions in a mass spectrum. This knowledge greatly reduces the number of possible compounds that could produce a particular mass spectrum. One can conclusively refute as candidate compounds those that provide similar low resolution mass spectra containing a molecular ion or a fragment ion with a different ion composition. Review of the chemical and commercial literature can further limit the probable identity of an analyte to one or a few compounds. However, in many cases the number of compounds with the same composition is large or the chemical classes of such compounds may represent multiple chemical classes. Thus, even when the list of candidates is reduced to only a few compounds, confirmation is time and resource intensive. In many cases the standards for possible candidates cannot be purchased and instead must be synthesized de novo which can be expensive and time consuming.

Therefore a need exists to improve the ability to elucidate the identity of an unknown compound by narrowing the list of candidate compounds to chemicals from the same biochemical class (e.g., amino acids, fatty acids, carbohydrates) and to further limit the candidates within a particular class.

BRIEF SUMMARY

In an aspect of the invention, a method of elucidating the identity of an unknown metabolite comprises measuring amounts of known and unknown metabolites in subjects; associating an unknown metabolite with a specific gene from a gene association study; determining a protein associated with the specific gene and analyzing information for the protein; associating the unknown metabolite with concentrations and/or ratios of other metabolites in subjects using a partial correlation network; obtaining chemical structural data for the unknown metabolite and deriving from the information obtained the identity of the unknown metabolite.

In a feature, the gene association study may be a genome wide association study. In another feature, the specific gene may comprise a single nucleotide polymorphism. In yet another feature, the method may further comprise reviewing the identity and/or characteristics of the other metabolites associated with the specific gene from the gene association study and/or identifying the biochemical pathway with which at least a portion of the other metabolites associated with the specific gene are involved.

In an additional feature, the chemical structural data may be obtained using mass spectrometry. The chemical structural data may also be obtained using nuclear magnetic resonance (NMR). The mass spectrometric data of the unknown metabolite may include mass, molecular formula, fragmentation spectra, and retention time. In a further feature, the information concerning the protein known to be associated with the gene may include function of the protein. In another feature, the protein may perform a metabolic function. The protein may be an enzyme. The substrate of the enzyme may be identified.

In another feature, the information for the protein may include the biochemical pathway for the protein substrate. Further, the information may include alternative biochemical pathways for the substrate. An alternative substrate of the enzyme may be determined. In an additional feature, the protein may be a transporter.

In yet another feature, reviewing the identity and/or characteristics of other metabolites associated with the specific gene from the gene association study and/or metabolites associated using the partial correlation network may include reviewing mass, class of compound, retention time, isotope patterns, fragments, and functionality of other metabolites. Further, the association between the protein and the gene may be the protein being encoded by the gene.

In another aspect of the invention, a method of elucidating the identity of an unknown metabolite comprises measuring amounts of known and unknown metabolites in subjects; associating an unknown metabolite with a specific gene from a gene association study; determining a protein associated with the specific gene and analyzing information for the protein; reviewing the identity and/or characteristics of the other metabolites associated with the specific gene from the gene association study; and/or identifying the biochemical pathway with which at least a portion of the other metabolites associated with the specific gene are involved; obtaining chemical structural data for the unknown metabolite; and deriving from the information obtained the identity of the unknown metabolite.

In yet another aspect of the invention, a method of elucidating the identity of an unknown metabolite comprises measuring amounts of known and unknown metabolites in subjects; associating an unknown metabolite with concentrations and/or ratios of other metabolites in the subjects using a partial correlation network; reviewing the identity and/or characteristics of the other metabolites associated with the unknown metabolite; and/or identifying the biochemical pathway with which at least a portion of the other metabolites associated with the unknown metabolite are involved; obtaining chemical structural data for the unknown metabolite; and deriving from the information obtained the identity of the unknown metabolite. In a feature of this aspect, the method may further comprise associating the unknown metabolite with a specific gene from a gene association study and determining a protein associated with the specific gene and analyzing information for the protein.

BRIEF DESCRIPTION OF THE DRAWINGS

The accompanying figures are included to provide a further understanding of the invention and are incorporated in and constitute a part of this application. In the figures.

DETAILED DESCRIPTION

Figure 1:
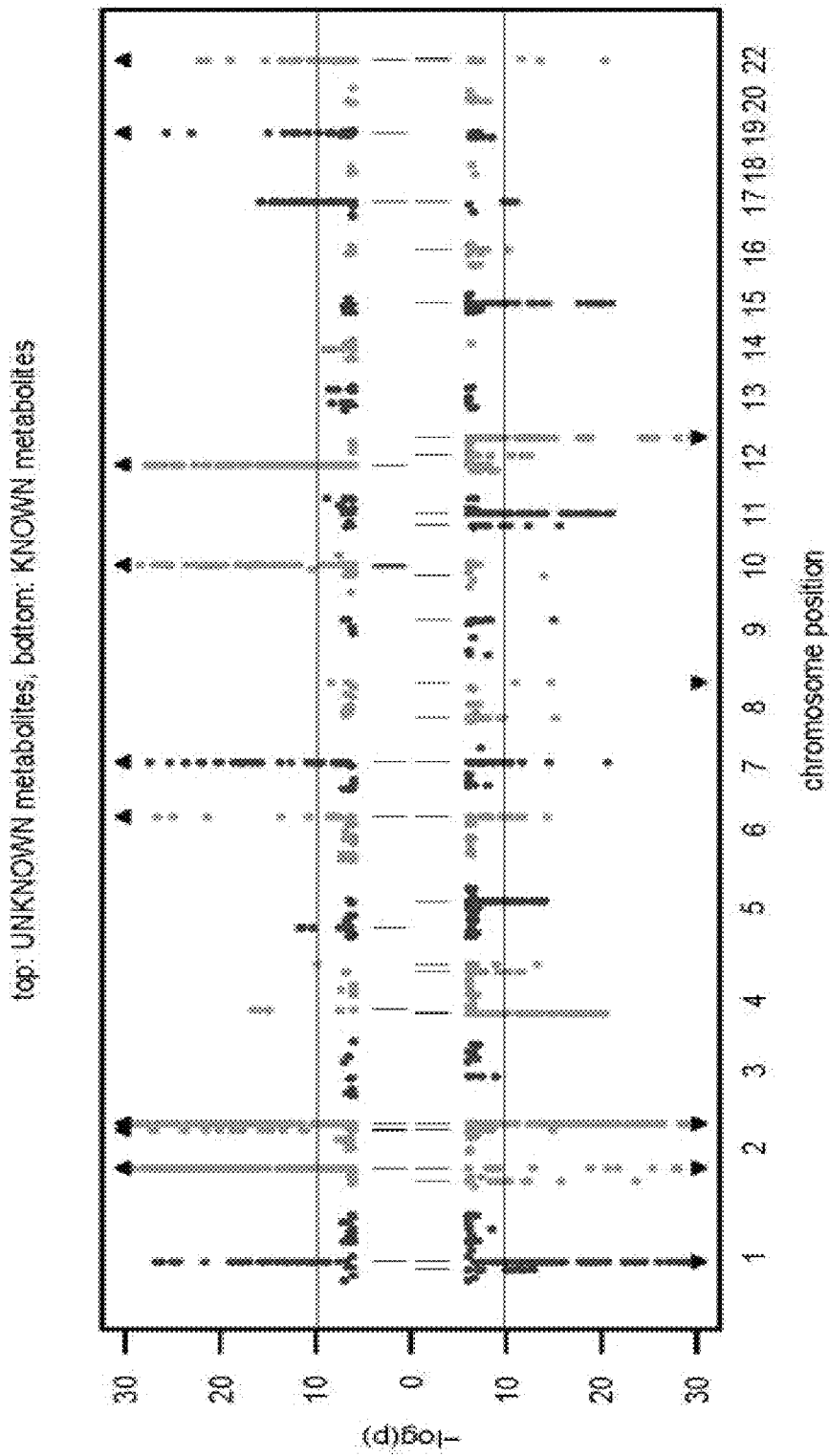
FIG. 1 is a Manhattan plot demonstrating the locations across the chromosomes of the human genome (on the X-axis) where there was a statistically significant association of the metabolites (knowns and unknowns). In the plot, the higher the dots, the stronger the genetic association.

The instant invention relates to a method whereby one or a plurality of unknown components (e.g., compounds, molecules, metabolites, biochemicals) can be identified. Biochemical analysis can be performed to aid in determining the identity of the unknown component. Biochemical analysis involves determining an association or relationship between two components (e.g., metabolites) using a correlation network. For example, a first variable showing a significant partial correlation to a second variable may be said to be associated with the second variable. Genetic analysis can also be used to aid in determining the identity of the unknown component. Genetic analysis includes using the association of the unknown component with a genetic locus or a genetic mutation. The association can be made using a genetic association study. A genetic association can be described as the occurrence of two or more traits in association with one another in a population, wherein at least one of the traits is known to be genetic and wherein the association occurs more often than can be explained by random chance. An exemplary genetic association study is a genome wide association study (GWAS). In addition, chemical structural data for the unknown component may be used to aid in determining the identity of the unknown. For example, data obtained from a mass spectrometer, such as accurate mass or ion fragment information, or data obtained from nuclear magnetic resonance may be used.

Information obtained from the biochemical analysis may be used with chemical structural data to aid in elucidating the identity of the unknown component. Information obtained from the genetic analysis may be used with chemical structural data to aid in elucidating the identity of the unknown component. Additionally, information obtained from both biochemical and genetic analysis may be combined and used with chemical structural data to aid in elucidating the identity of the unknown component.

With regard to the genetic analysis, the association of an unknown component with a gene or a genetic polymorphism can reveal the type of reaction in which the unknown component is involved. For example, GWAS analysis between single nucleotide polymorphisms (SNPs) and an unknown component can be used to reveal the type of reaction (for example, methylation) in which the unknown component is involved. As will be understood by one of ordinary skill in the art, the association of an unknown component with a gene or a genetic polymorphism can provide valuable information in determining the identity of the unknown component.

In an exemplary embodiment, metabolic data (for example, the amount of known and unknown metabolites) may be obtained from biological samples taken from subjects in a population group. For the genetic analysis, the metabolic data can be used to associate an unknown metabolite with a genetic locus or a genetic mutation. One of ordinary skill in the art will understand that genotype information for the subjects is also used in making the genetic association. For biochemical analysis, the metabolic data can be used to determine associations between various metabolites using partial correlation networks, which are also called Gaussian Graphical Models (GGMs). Using the GGMs, an association between metabolites represents a partial correlation between the metabolites. A network can be built by drawing connections for metabolites that are associated. The network can provide an estimate for a pathway in which an unknown metabolite is involved.

In an example wherein the genetic association study is a GWAS, results from the biochemical analysis and the GWAS can be combined to aid in determining the identity of the unknown component. In addition to the information obtained from biological samples for the particular subject pool, publicly available metabolic pathway data can also be used to further narrow the list of possible components. Thus, using genetic and biochemical information and publicly available information enables reducing the list of potential components for an unknown component, keeping only those components that play a role in the biochemical context given by the partial correlation network and that could, at the same time, be direct or indirect substrates or products of the specified enzymatic reaction, as determined using the genetic information. Additionally, chemical structural analysis can be performed to aid in determining the identity of the unknown component. For example, mass spectrometry (MS) data (e.g., accurate mass and chemical formula) for the reduced list of potential unknown components can be compared with that of known components to help determine the identity of the unknown component. While the exemplary genetic association study discussed herein is a GWAS, one of ordinary skill in the art will understand and appreciate that the data used in determining the identity of an unknown component can be obtained with other types of genetic association studies.

Genome Wide Association Study

A GWAS is an example of a genetic association study. In a GWAS, a plurality of genes is interrogated for their association with a phenotype. In other types of genetic association studies, the same type of association can be done with a single genetic locus. GWAS have been used to identify hundreds of disease risk loci.

In a GWAS, the density of genetic markers and the extent of linkage disequilibrium are sufficient to capture a large proportion of the common variation in the human genome in the population under study, and the number of specimens genotyped provides sufficient power to detect variants of modest effect. GWAS can be conducted to rapidly and cost-effectively analyze genetic differences between people with specific illnesses, such as diabetes or heart disease, compared to healthy individuals. The studies can explore the connection between specific genes, known as genotype information, and their observable characteristics or traits, known as phenotype information, and can facilitate the identification of genetic risk factors for the development or progression of disease. It will be understood that disease status is an exemplary phenotype. It will also be understood that a GWAS or other genetic association study may be used to analyze data related to any phenotype. Phenotypes can be binary (e.g., diseased or healthy) or can be continuous variable (e.g., BMI, weight, blood pressure). Exemplary continuous variable phenotypes include blood pressure, BMI, height, metabolite concentration, and medication being taken.

The GWAS takes an approach that involves rapidly scanning markers (such as, a genetic polymorphism (for example, a SNP)) across the complete sets of DNA, or genomes, of many people to find genetic variations associated with a particular phenotype (e.g., disease). In the example wherein the phenotype is a disease, once new genetic associations are identified, researchers can use the information to develop better strategies to detect, treat and prevent the disease being studied. Such studies are particularly useful in finding genetic variations that contribute to common, complex diseases, such as asthma, cancer, diabetes, heart disease and mental illnesses. More specific details regarding performing a GWAS will be described below. One of ordinary skill in the art will understand that many of the steps performed in a GWAS are also used in other types of genetic association studies, but typically on a smaller scale because the entire genome is not being scanned.

To carry out a GWAS, researchers characterize the participants by a phenotype (e.g., diseased vs. non-diseased). Researchers obtain DNA from each participant, usually by drawing a blood sample or by rubbing a cotton swab along the inside of the mouth to harvest cells.

Each person's DNA is then purified from the blood or cells, placed on genotyping chips comprised of genetic markers representing the entire genome and scanned on automated laboratory instruments. In a smaller scale genetic association study, a smaller subset of genetic markers would be analyzed. The instruments survey each participant's genome for the presence of markers of genetic variation. A genetic marker is a DNA sequence with a known location on a chromosome with a variation that can be observed. A genetic marker may be a short DNA sequence comprised of a single nucleotide difference or it may be a longer one such as a repeating sequence of DNA or DNA sequence insertions or sequence deletions. The most widely used genetic markers are called single nucleotide polymorphisms, or SNPs. Other types of genetic markers include AFLPs (Amplified Fragment Length Polymorphisms), RFLPs (Restriction Fragment Length Polymorphisms), SSLP (Simple Sequence Length Polymorphisms), RAPDs (Random Amplification of Polymorphic DNA) and CAPS (Cleaved Amplified Polymorphisms).

If certain genetic variations are found to be significantly more frequent or less frequent in people showing a phenotype (e.g., the disease) compared to people lacking this phenotype (e.g., without the disease), the variations are said to be "associated" with the phenotype (e.g., disease). The associated genetic variations can serve as pointers to the region of the human genome where the phenotype-causing problem resides.

The associated variants themselves may not directly cause the disease. They may just be "tagging along" with the actual causal variants. For this reason, researchers often need to take additional steps, such as sequencing DNA base pairs in the particular region of the genome, to identify the exact genetic change involved in the disease.

Genetically determined metabotypes (GDMs) are identified using genetic associations with metabolites measured in biological samples (e.g., blood, urine, tissue) as functional intermediate phenotypes, and facilitate the ability to understand the relevance of these genetic variants for biomedical and pharmaceutical research.

Information obtained using data from a genetic association study can be used for various purposes. For example, the information obtained can be used to associate an unknown biochemical with a SNP and the associated genetic locus. The information can be used to identify an unknown biochemical based upon the function of the protein encoded by the identified gene. The information can be used to associate a known metabolite with the same SNP and locus, which can facilitate identification of biochemical pathways for the unknown biochemical and identification of the unknown biochemical.

Partial Correlation Networks (Gaussian Graphical Models)

Gaussian graphical models (GGMs) are partial correlation networks, which can provide an estimate for the pathway in which an unknown component (e.g., a metabolite) is involved. For example, GGMs can be used to determine metabolic pathway reactions using metabolic concentrations measured for a sample population. Characteristic patterns in metabolite profiles can be directly linked to underlying biochemical reaction networks. In the GGM, a connection between two variables (e.g., metabolites) represents a so-called partial correlation between the variables. A GGM can be represented by drawing metabolite-metabolite connections for pairs of metabolites (knowns or unknowns) that show a significant partial correlation. Connections based on known reaction links between two metabolites based on public metabolic databases can be added to the network representation to provide more identifying information. Considering the neighboring known metabolites of an unknown in the network provides a good estimate for the pathway in which the unknown is involved.

Gaussian graphical models are created using full-order partial correlation coefficients. The partial correlation coefficient between two variables is given by the Pearson correlation coefficient corrected against all remaining (n−2) variables. Intuitively speaking, the partial correlation means that if a pair of metabolites is still correlated after the correction, the correlation is directly determined by the association of the two metabolites and not mediated by other metabolites in the data set. For example, when metabolite A directly affects metabolite B and metabolite B directly affects metabolite C, A and C are also correlated in terms of a non-partial correlation. However, A and C are not correlated after correcting for the correlations between A/B and B/C.

By focusing on direct effects between metabolites, GGMs group metabolites by their biochemical context when applied to targeted metabolomics data. In the present method, a GGM is used with non-targeted metabolomics data containing both known and unknown metabolites. Hence, in order to estimate the biochemical context of an unknown metabolite using the GGM, the context or pathway in which the known metabolites neighboring the unknown metabolite are involved is considered. For facilitating network interpretation, connections based on known reaction links between two metabolites according to metabolic databases such as the KEGG PATHWAY database can be added.

Gaussian graphical models use linear regression models and are able to discern indirect correlations between metabolites that do not indicate an independent association between the metabolites. Any indirect correlations can be removed from the analysis.

In an exemplary embodiment, a method of elucidating the identity of an unknown metabolite comprises measuring amounts of known and unknown metabolites; associating an unknown metabolite with a specific gene from a gene association study; determining a protein associated with the specific gene and analyzing information for the protein; associating the unknown metabolite with concentrations and/or ratios of other metabolites using a partial correlation network; obtaining chemical structural data for the unknown metabolite; and using the information obtained in order to elucidate the identity of the unknown metabolite. Measuring the amounts of known and unknown metabolites comprises analysis a biological sample (e.g., tissue, blood, or urine) to measure the amounts of the metabolites.

EXAMPLES

In order to identify candidate molecules for unidentified molecular entities that were repeatedly observed in MS-based metabolomics measurements, information gained from the application of two different methods on the same population-based sample set was integrated: (i) genome-wide association analysis between single nucleotide polymorphisms (SNPs) and the MS-based quantitative measurements of the aforementioned known and unidentified molecular entities (in this example, the entities are metabolites), and (ii) partial correlation networks (Gaussian Graphical Models) calculated from the quantitative measurements of known as well as unidentified molecular entities (in this example, the entities are metabolites). The study was based on genome-wide SNP data for a population-based cohort and the quantities measured for known and yet unknown molecules by UPLC-MS/MS or GC-MS in blood serum samples from the same cohort. In this study, the population-based cohort was 1768 individuals comprising 859 male and 909 female genotyped individuals, who were aged 32-81 years at the time of sampling.

In the study, over 250 known biochemicals were analyzed in 60 biochemical pathways in 1700+ serum samples. In addition, over 200 unknown biochemicals were quantified in these samples. Metabolic profiling was performed on fasting serum from participants of the study (n=1,768) using ultra-high performance liquid-phase chromatography and gas chromatography separation coupled with tandem mass spectrometry. Highly efficient profiling (24 minutes/sample) was achieved with low median process variability (12%) of more than 250 metabolites, covering over 60 biochemical pathways of human metabolism.

While the examples describe an approach wherein the entire genome for the subjects was studied, one of ordinary skill in the art will understand that the same type of analysis can be performed for individual genes or individual genetic polymorphisms. Additionally, one of ordinary skill in the art will understand that the sequence of the steps of the analysis process may vary. Such variation is within the scope of the invention.

Genome-Wide Associations

SNP data: Genotyping was carried out using the Affymetrix GeneChip array 6.0. For the analyses, only autosomal SNPs passing the following criteria were considered: call rate >95%, Hardy-Weinberg-Equilibrium p-value $p(HWE)>10^{-6}$, minor allele frequency MAF>1%. In total, 655,658 SNPs were left after filtering.

Molecule quantities: The blood serum samples of the 1768 genotyped individuals were screened on known metabolomics platforms (UPLC-MS/MS, GC-MS) providing the relative quantities of (295) known and (224) unknown metabolites in these samples. In order to avoid spurious false positive associations due to small sample sizes, only metabolic traits with at least 300 non-missing values were included and datapoints of metabolic traits that lay more than 3 standard deviations off the mean were excluded by setting them to missing in the analysis. 274 known and 212 unknown metabolites passed this filter.

Statistical analysis: The metabolite quantities were log-transformed since a test of normality showed that in most cases the log-transformed distribution was significantly better represented by a normal distribution than when untransformed values were used. The genotypes are represented by 0, 1, and 2 for major allele homozygous, heterozygous, and minor allele homozygous, respectively.

A linear model was employed to test for associations between a SNP and a metabolite assuming an additive mode of inheritance. The tests were carried out using PLINK software (version 1.06) with age and gender as covariates. Based on a conservative Bonferroni correction, associations with p-values $<1.6 \times 10^{-10}$ meet genome-wide significance. For significant associations of a metabolite (known and unknown) with SNPs within a distance of $10^6$ nucleotides, only the most significant association is reported in Table 1. Table 2 lists all unknown metabolite-SNP associations with p-values below $1 \times 10^{-5}$. Thus, in contrast to Table 1, Table 2 includes (i) associations not reaching genome-wide significance and (ii) all associations rather than only the most significant ones for the $10^{-6}$ nucleotides window.

The SNPs involved in the most significant associations of SNPs and/or the SNPs in the linkage disequilibrium of the association SNPs with known metabolites have shown to be mostly within or close to genes whose function 'matches' the metabolite (e.g., association of a SNP in the gene encoding oxoprolinase with oxoproline quantities). This effect can thus be used to narrow the set of candidate molecules in case of unknown metabolites. For example, this effect can be used for estimating the type of enzymatic conversion (or transport) to which an unknown is related. For this purpose, we performed a GWAS on quantities of the unknown (and known) metabolites from the metabolomics data set described above. In case of significant SNP-unknown associations for which the SNP is located close to or within a gene, the genetic information (such as the substrate specificity of the encoded enzyme or transporter) was used as a constraint for reducing the number of candidate molecules. FIG. 1 is a Manhattan plot for the known and unknown metabolites showing a circle for each metabolite-SNP pair for which the p-value of their association is below $1.0 \times 10^{-6}$. The black horizontal line denotes the limit of genome-wide significance. The black triangles represent all associations with p-values lower than $1.0 \times 10^{-30}$. The associations of unknown metabolites are plotted in the upper part, the associations of known metabolites are plotted in the lower part of the figure. Table 1 provides a list of metabolites and SNPs with which the metabolites were associated most significantly, in particular, within a window of $10^6$ nucleotides. The SNPs are listed along with their position on the genome (CHR: chromosome; Position: position on the chromosome (base pairs)) and the gene that was annotated for the associating SNP or SNPs within the linkage disequilibrium (LD) using an LD criterion of $r^2>0.8$. Moreover, the number of samples is given for which data on the amount of the metabolite and data on the genotype was available. The columns BETA and P (p-value) contain the results of the additive linear model that was used for testing the association between the metabolite and the SNP. Only genome-wide significant associations are shown in Table 1. Table 2 provides a list of all unknown metabolite-SNP associations with p-values below $1\times10^{-5}$. Table 3 provides a list of unknown metabolites and shows the metabolite neighbors of the unknown as determined with the GGM network and the best associating SNP for the unknown as determined with the GWAS. Because of size considerations, Tables 2 and 3 are at the end of this description.

TABLE 1

| CHR | POSITION | SNP | GENE in LD >0.8 | METABOLITE | #SAMPLES | BETA | P |
|---|---|---|---|---|---|---|---|
| 1 | 47170815 | rs1078311 | CYP4A11 | 10-undecenoate (11:1n1) | 1744 | 0.05602 | 1.47E-013 |
| 1 | 75910194 | rs12134854 | ACADM | hexanoylcarnitine | 1732 | -0.08111 | 4.97E-043 |
| 1 | 75910194 | rs12134854 | ACADM | octanoylcarnitine | 1735 | -0.08345 | 2.57E-036 |
| 1 | 75910194 | rs12134854 | ACADM | X11421 | 1721 | -0.07391 | 1.90E-027 |
| 1 | 75879263 | rs211718 | ACADM | decanoylcarnitine | 1736 | -0.06534 | 3.77E-021 |
| 2 | 27594741 | rs780094 | GCKR | mannose | 1702 | -0.04725 | 2.06E-024 |
| 2 | 73506136 | rs7598396 | ALMS1 | N-acetylornithine | 1717 | -0.2137 | 1.30E-149 |
| 2 | 73506136 | rs7598396 | ALMS1 | X12510 | 1697 | -0.1317 | 1.53E-056 |
| 2 | 73673616 | rs6710438 | NAT8 | X11787 | 1722 | -0.04063 | 2.95E-037 |
| 2 | 73672444 | rs13391552 | NAT8 | X12093 | 948 | 0.1114 | 8.86E-022 |
| 2 | 210768295 | rs2286963 | ACADL | X13431 | 1453 | 0.09672 | 2.68E-033 |
| 2 | 211325139 | rs2216405 | CPS1 | glycine | 1721 | 0.04127 | 1.28E-015 |
| 2 | 234333309 | rs887829 | UGT1A | biliverdin | 1123 | 0.1023 | 5.53E-047 |
| 2 | 234333309 | rs887829 | UGT1A | bilirubin (Z,Z) | 1646 | 0.1551 | 1.33E-046 |
| 2 | 234337378 | rs6742078 | UGT1A | X11530 | 1701 | 0.08613 | 2.12E-038 |
| 2 | 234337378 | rs6742078 | UGT1A | X11441 | 1584 | 0.08834 | 5.59E-030 |
| 2 | 234333309 | rs887829 | UGT1A | X11793 | 1539 | 0.07591 | 2.59E-026 |
| 2 | 234337378 | rs6742078 | UGT1A | X11442 | 1584 | 0.08056 | 1.19E-025 |
| 2 | 234333309 | rs887829 | UGT1A | bilirubin (E,E) | 1694 | 0.0939 | 3.04E-024 |
| 4 | 9611763 | rs9991278 | SLC2A9 | urate | 1706 | -0.02992 | 4.64E-021 |
| 4 | 22429602 | rs358231 | GBA3 | X11799 | 1481 | 0.1373 | 2.87E-017 |
| 4 | 159850267 | rs8396 | ETFDH | decanoylcarnitine | 1711 | -0.05031 | 2.35E-012 |
| 4 | 187394452 | rs4253252 | KLKB1 | bradykinin, des-arg(9) | 1463 | 0.09777 | 5.93E-014 |
| 5 | 36025563 | rs13358334 | UGT3A1 | X11445 | 1642 | 0.08772 | 2.36E-012 |
| 5 | 131693277 | rs272889 | SLC22A4 | isovalerylcarnitine | 1725 | 0.04099 | 9.18E-015 |
| 5 | 131689055 | rs273913 | SLC22A4 | 3-dehydrocarnitine | 1682 | 0.0298 | 1.62E-011 |
| 6 | 160589071 | rs316020 | SLC22A2 | X12798 | 1629 | -0.1748 | 1.73E-072 |
| 6 | 160484466 | rs662138 | SLC22A1 | isobutyrylcarnitine | 1700 | -0.06786 | 5.41E-015 |
| 7 | 99078115 | rs10242455 | CYP3A5 | X12063 | 1660 | -0.2485 | 1.47E-045 |
| 7 | 99327507 | rs17277546 | CYP3A4 | androsterone sulfate | 1728 | -0.2435 | 2.08E-021 |
| 7 | 99327507 | rs17277546 | CYP3A4 | epiandrosterone sulfate | 1729 | -0.1717 | 3.35E-015 |
| 8 | 18317580 | rs1495743 | NAT2 | 1-methylxanthine | 1148 | -0.09426 | 6.10E-016 |
| 8 | 145211510 | rs6558295 | OPLAH | 5-oxoproline | 1734 | -0.0611 | 8.36E-051 |
| 9 | 135143696 | rs651007 | ABO | ADpSGEGDFXAEGGGVR | 1692 | 0.06719 | 1.00E-015 |
| 10 | 61119570 | rs7094971 | SLC16A9 | carnitine | 1724 | -0.02185 | 1.06E-014 |
| 10 | 85443900 | rs12413935 | | X06226 | 1722 | -0.05911 | 4.09E-011 |
| 10 | 96454720 | rs7896133 | CYP2C18 | X11787 | 1738 | -0.05619 | 3.97E-026 |
| 10 | 100149126 | rs4488133 | PYROXD2 | X12092 | 1711 | -0.2842 | 2.24E-281 |
| 10 | 100149126 | rs4488133 | PYROXD2 | X12093 | 948 | -0.1252 | 1.35E-027 |
| 11 | 18281722 | rs2403254 | HPS5 | alpha-hydroxyisovalerate | 1733 | -0.05239 | 2.60E-016 |
| 11 | 61327924 | rs174548 | FADS1 | arachidonate (20:4n6) | 1730 | -0.0414 | 9.98E-022 |
| 11 | 61327359 | rs174547 | FADS1 | 1-arachidonoylglycerophosphocholine | 1584 | -0.05788 | 2.54E-020 |
| 11 | 61327359 | rs174547 | FADS1 | 1-linoleoylglycerophoethanolamine | 1733 | 0.04499 | 1.94E-014 |
| 11 | 61366326 | rs174583 | FADS1 | 1-arachidonoylglycerophoethanolamine | 1699 | -0.03864 | 2.37E-013 |
| 11 | 61327359 | rs174547 | FADS1 | eicosapentaenoate (EPA; 20:5n3) | 1730 | -0.04007 | 1.49E-010 |
| 12 | 21222816 | rs4149056 | SLCO1B1 | X11529 | 1138 | 0.2564 | 3.28E-081 |
| 12 | 21222816 | rs4149056 | SLCO1B1 | X11538 | 1736 | 0.1087 | 1.35E-037 |
| 12 | 21222816 | rs4149056 | SLCO1B1 | X13429 | 1230 | 0.141 | 4.86E-022 |
| 12 | 21222816 | rs4149056 | SLCO1B1 | X12063 | 1660 | 0.1016 | 5.22E-020 |
| 12 | 21222816 | rs4149056 | SLCO1B1 | X12456 | 1260 | 0.08351 | 8.41E-017 |
| 12 | 21269288 | rs4149081 | SLCO1B1 | X14626 | 1235 | 0.08085 | 2.08E-013 |
| 12 | 55151605 | rs2657879 | GLS2 | glutamine | 1732 | -0.01542 | 3.21E-013 |
| 12 | 119644998 | rs2066938 | ACADS | butyrylcarnitine | 1682 | 0.1983 | 3.73E-177 |
| 15 | 61209825 | rs2652822 | LACTB | succinylcarnitine | 1474 | -0.04431 | 1.05E-021 |
| 16 | 66883701 | rs6499165 | SLC7A6 | glutaroyl carnitine | 1675 | 0.03404 | 6.49E-011 |
| 17 | 58919763 | rs4343 | ACE | X14189 | 1703 | -0.05975 | 1.48E-016 |
| 17 | 58923464 | rs4351 | ACE | X14208 | 1628 | -0.05775 | 4.58E-015 |
| 17 | 58923464 | rs4351 | ACE | X14205 | 1470 | -0.04795 | 3.97E-014 |
| 17 | 58916932 | rs4325 | ACE | X14304 | 1467 | -0.05359 | 2.68E-012 |
| 17 | 58916932 | rs4325 | ACE | aspartylphenylalanine | 1688 | -0.06079 | 1.05E-011 |
| 19 | 53060346 | rs296391 | SULT2A1 | X11440 | 1685 | -0.1494 | 1.69E-043 |
| 19 | 53060346 | rs296391 | SULT2A1 | X11244 | 1676 | -0.1464 | 2.12E-026 |

TABLE 1-continued

| CHR | POSITION | SNP | GENE in LD >0.8 | METABOLITE | #SAMPLES | BETA | P |
|---|---|---|---|---|---|---|---|
| 22 | 17352450 | rs2023634 | PRODH | proline | 1733 | 0.05435 | 4.32E−021 |
| 22 | 18331271 | rs4680 | COMT | X11593 | 1712 | 0.04945 | 1.13E−048 |
| 22 | 18331271 | rs4680 | COMT | X01911 | 1626 | 0.07037 | 5.80E−011 |
| 22 | 23322266 | rs5751901 | GGT1 | cysteine-glutathione disulfide | 1598 | −0.05311 | 2.50E−012 |

Partial Correlation Networks (Gaussian Graphical Models)

In this example, a network was built by drawing metabolite-metabolite connections for pairs of metabolites (knowns or unknowns) that showed a significant partial correlation. To do this network connections based on known reaction links between two metabolites based on public metabolic databases were added. Considering the neighboring known metabolites of an unknown in the network provides a good estimate for the pathway in which the unknown is involved.

The blood serum samples of all 1768 individuals were screened to provide the relative quantities of (295) known and (224) unknown metabolites in the samples. For the calculation of the GGM, the following data preprocessing was applied. All metabolites with more than 20% missing values and all samples with more than 10% missing values were excluded. Remaining missing values were imputed using MICE. MICE stands for Multivariate Imputation by Chained Equations. MICE is a software program used to impute missing values. Multiple imputation is a statistical technique for analyzing incomplete data sets, that is, data sets for which some entries are missing.

Gaussian graphical models were induced by full-order partial correlation coefficients. Additionally, correction was made for SNPs with significant associations to metabolites in the GWAS. Thus, it was expected that the remaining correlations between metabolites were not mediated by metabolite-SNP associations.

By focusing on direct effects between metabolites, GGMs group metabolites by their biochemical context when applied to targeted metabolomics data. In the present method, a GGM is used with non-targeted metabolomics data containing both known and unknown metabolites. Hence, in order to estimate the biochemical context of an unknown metabolite using the GGM, the context or pathway in which the known metabolites neighboring the unknown metabolite are involved is considered. For facilitating network interpretation, connections based on known reaction links between two metabolites according to metabolic databases such as the KEGG PATHWAY database were added.

Gaussian graphical models utilize linear regression models and are thus able to discern indirect correlations between metabolites that do not indicate an independent association between those metabolites and thus remove any indirect correlations from the analysis. If the dataset contained more samples than variables, full-order partial correlations were calculated by a matrix inversion operation. First, regular Pearson product-moment correlation coefficients $\rho_{ij}$ were calculated as:

$$P = (\rho_{ij}) = \frac{\sum_{k=1}^{n}(x_{ki} - \bar{x}_i)(x_{kj} - \bar{x}_j)}{\sqrt{\sum_{k=1}^{n}(x_{ki} - \bar{x}_i)^2} \cdot \sqrt{\sum_{k=1}^{n}(x_{kj} - \bar{x}_j)^2}}$$

Next, partial correlation coefficients were computed as the normalized, negative matrix inverse of this correlation:

$$Z = (\zeta_{ij}) = -\omega_{ij}/\sqrt{\omega_{ii}\omega_{jj}} \text{ with } (\omega_{ij}) = P^{-1}$$

P-values $p(\zeta_{ij})$ for each partial correlation were obtained using Fisher's z-transform:

$$z(\zeta_{ij}) = \frac{1}{2}\ln\left(\frac{1+\zeta_{ij}}{1-\zeta_{ij}}\right),$$

$$p(\zeta_{ij}) = \left(1 - \phi\left(\sqrt{n-(m-2)-3} \cdot z(\zeta_{ij})\right)\right)$$

where $\phi$ stands for the cumulative distribution function of the standard normal distribution. In order to account for multiple hypothesis testing, we applied Bonferroni correction, yielding a corrected significance level of $$\hat{\alpha} := \frac{0.05}{n(n-1)/2}.$$

Adding connectors from known reactions: Metabolic reactions were imported from three independent human metabolic reconstruction projects: (1) *H. sapiens* Recon 1 from the BiGG databases (Duarte, et al., 2007), (2) the Edinburgh Human Metabolic Network (EHMN) reconstruction (Ma, et al., 2007) and (3) the KEGG PATHWAY database (Kanehisa & Goto, 2000) as of January 2011.

When adding connectors from known reactions to the GGM, an accurate mapping between the different metabolite identifiers of the respective databases and the identifiers used in the quantitative metabolite data was created. As one of ordinary skill in the art will appreciate, differing forms of biochemical components can represent the same biochemical entity with regard to biochemical pathway. For example, despite the fact that the salt form and the acid form of a metabolite have different names, the salt form of a metabolite will function biochemically the same as the acid form of the metabolite. Accordingly, metabolite identifiers rather than just chemical names are used to create accurate mapping. Database entries referring to whole groups of metabolites, like "phospholipid", "fatty acid residue" or "proton acceptor" were excluded. Furthermore, metabolic cofactors like "ATP", "$CO_2$", and "$SO_4$", etc. were not considered in the analysis, since such metabolites unspecifically participate in a plethora of metabolic reactions.

Combining the GGM and GWAS Results

After the GGM step, a good estimate on the biochemical context of an unknown was obtained. After the GWAS, a good estimate of the enzymatic reaction or transport in which the unknown was directly or indirectly involved was obtained. Once this information was available, it was used to exclude or favor molecules from the list of molecules having a mass that matches a mass measured for the unknown. Additional information provided by mass spectrometry can be used to aid in determining the identity of the unknown. For example, ion fragmentation information can be used. In the following, we demonstrate the procedure by giving two examples.

Example 1

Previously unidentified biomarker X-14205 was identified using the following procedure.

The mass of the unknown X-14205 was determined in a LC/MS/MS run in positive ionization mode. The mass quantified for this unknown was 311.1.

Following the GGM steps described above, a GGM network for X-14205 was obtained. Metabolites shown to have significant partial correlations to X-14205 are listed in Table 4.

TABLE 4

Metabolites having significant partial correlation with the unknown metabolite X-14205.

| Unknown: | Significant partial correlation to: | p-value |
|---|---|---|
| X-14205 | X-14478 | 4.22E−87 |
| | DSGEGDFXAEGGGVR (SEQ ID No. 1) | 1.89E−35 |
| | Cysteine glutathione disulfide | 9.59E−33 |
| | X-14208 | 2.25E−24 |
| | X-11805 | 1.49E−17 |
| | X-06307 | 2.24E−16 |
| | X-14086 | 1.34E−12 |
| | X-14450 | 1.73E−12 |
| | ADSGEGDFXAEGGGVR (SEQ ID No. 2) | 3.29E−09 |
| | aspartate | 6.52E−09 |
| | phenylalanine | 3.18E−07 |
| | glutamate | 4.19E−07 |
| | ADpSGEGDFXAEGGGVR (SEQ ID No. 3) | 6.26E−07 |

Figure 2:
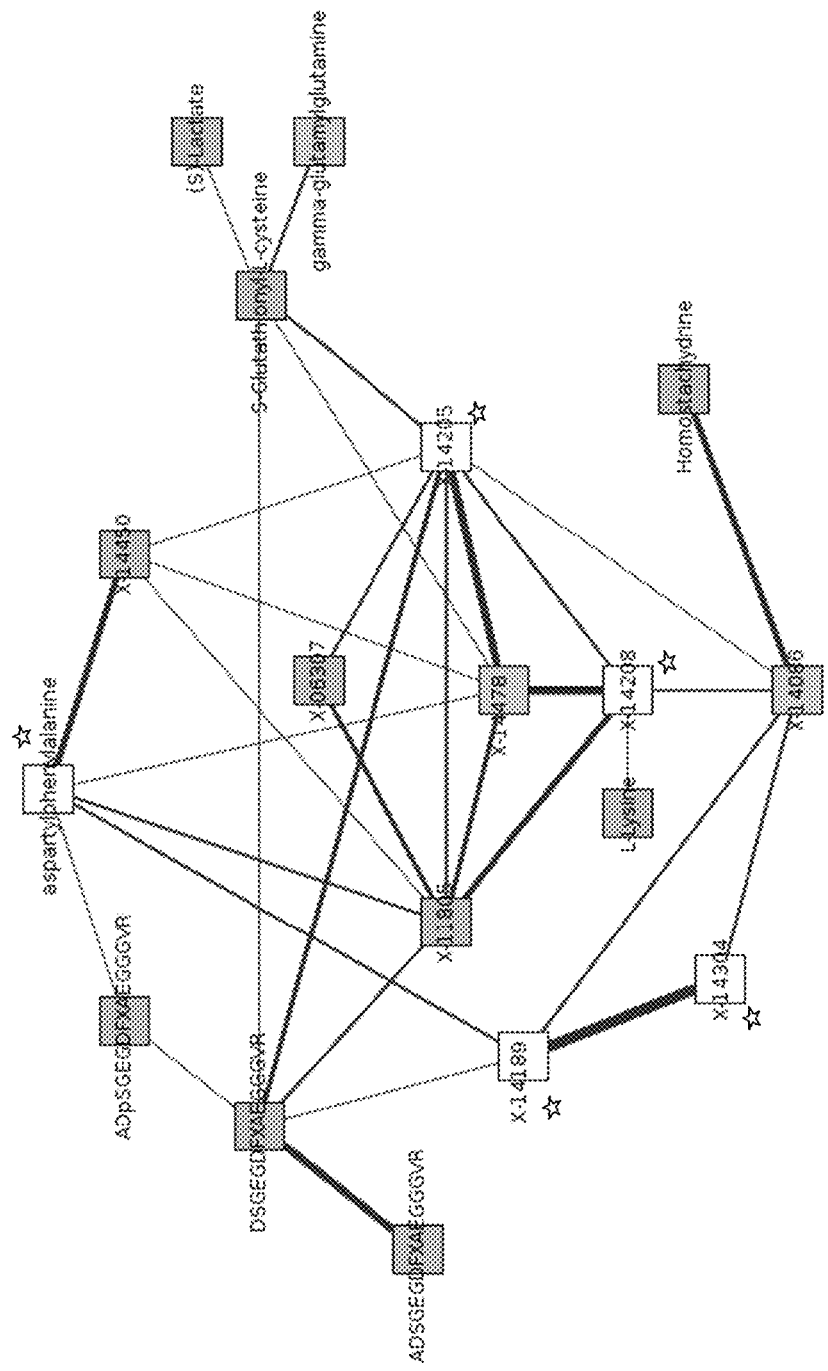
FIG. 2 is a graphical representation of a Gaussian Graphical Model (GGM) network showing the most significant direct and second neighbors of X-14205, X-4208 and X-14478.

FIG. 2 provides a GGM network showing the most significant direct and second neighbors of X-14205. Therein, the connectors connect significantly partially correlating metabolites. The connectors are weighted by the degree of significance (specifically, the lower the p-value of the correlation, the thicker the line). In FIG. 2, the starred (*) metabolites denote those that show a significant association with a SNP in the ACE gene.

For X-14205, checking for known reactions from metabolic databases did not provide additional connectors within a distance of two from the unknown. The majority of known metabolites occurring in the GGM of X-14205 are peptides, dipeptides, and amino acids.

In the GWAS analysis, X-14205 was found to associate most significantly with a SNP in the gene encoding the angiotensin I converting enzyme (ACE). This enzyme is known to cut a dipeptide off from the oligopeptide angiotensin I as well as from further oligopeptides. Table 5 shows the most significant hit that was found in the GWAS analysis for X-14205.

TABLE 5

Most significant hit in the GWAS for the unknown X-14205.

| Unknown | Best Assoc. SNP | Locus | Enzyme | p-value |
|---|---|---|---|---|
| X-14205 | rs4351 | ACE | angiotensin I converting enzyme | 3.97E−14 |

When the results from the GGM and the GWAS were integrated, it appeared that besides X-14205, the dipeptide aspartylphenylalanine and the unknowns X-14208, X-14189, and X-14304, were also significantly associated with SNPs in ACE. (In FIG. 2 all metabolites associating with ACE SNPs are marked by a starred (*) box.) It was hypothesized that X-14205 is a dipeptide (and also X-14208, X-14189, X-14304). Considering the mass of X-14205, the most probable candidates were Glu-Tyr or Tyr-Glu.

In order to experimentally confirm the hypothesis, the accurate mass of X-14205 was determined. Its neutral mass 310.11712 supported the formula $C_{14}H_{18}N_2O_6$, which also fits the two hypothesized dipeptides. For experimental validation, Glu-Tyr and Tyr-Glu from a commercial source were run on a proprietary LC/MS/MS platform. The retention time and the fragmentation spectrum received for Glu-Tyr matched the time and spectrum of X-14205. Thus, using the above-described method, X-14205 was identified by testing only two candidate molecules.

Example 2

Previously unidentified biomarker X-14208 was identified using the following procedure.

The mass of the unknown X-14208 was determined in a LC/MS/MS run in positive ionization mode. The mass quantified for this unknown was 253.1.

Following the GGM steps described above, a GGM network for X-14208 was obtained. Metabolites shown to have significant partial correlations to X-14208, are listed in Table 6.

TABLE 6

Metabolites having significant partial correlation with the unknown metabolite X-14208.

| Unknown: | Significant partial correlation to: | p-value |
|---|---|---|
| X-14208 | X-14478 | 4.67E−153 |
| | X-11805 | 6.14E−62 |
| | X-14205 | 2.25E−24 |
| | X-14086 | 1.83E−14 |
| | lysine | 5.68E−11 |

FIG. 2 provides a GGM network showing the most significant direct and second neighbors of X-14208. Therein, the connectors connect significantly partially correlating metabolites. The connectors are weighted by the degree of significance (specifically, the lower the p-value of the correlation, the thicker the line). In FIG. 2, the starred (*) metabolites denote those that show a significant association with a SNP in the ACE gene.

For X-14208, checking for known reactions from metabolic databases did not provide additional connectors within a distance of two from the unknown. The majority of known metabolites occurring in the GGM of X-14208 are peptides, dipeptides, and amino acids.

In the GWAS analysis, X-14208 was found to associate most significantly with a SNP in the gene encoding the angiotensin I converting enzyme (ACE). This enzyme is known to cut a dipeptide off from the oligopeptide angiotensin I as well as from further oligopeptides. Table 7 shows the most significant hit from the GWAS analysis for X-14208.

TABLE 7

Most significant hit in the GWAS for the unknown X-14208.

| Unknown | Best Assoc. SNP | Locus | Enzyme | p-value |
|---|---|---|---|---|
| X-14208 | rs4351 | ACE | angiotensin I converting enzyme (peptidyl-dipeptidase A) 1 | 4.58E−15 |

When the results from the GGM and the GWAS were integrated, it appeared that besides X-14208, the dipeptide aspartylphenylalanine and the unknowns X-14205, X-14189, and X-14304, were also significantly associated with SNPs in ACE. (In FIG. 2 all metabolites associating with ACE SNPs are marked by a starred (*) box.) It was hypothesized that X-14208 is a dipeptide (and also X-14205, X-14189, X-14304). Considering the mass of X-14208, the most probable candidates were Phe-Ser or Ser-Phe.

In order to experimentally confirm the hypothesis, the accurate mass of X-14208 was determined. Its neutral mass 252.11172 supported the formula $C_{12}H_{16}N_2O_4$, which also fits the two hypothesized dipeptides. The formula matches more than 1,200 molecular structures, but the prediction of this unknown as a dipeptide narrowed the field to only the two candidate molecules for validation. For experimental validation, Phe-Ser and Ser-Phe from a commercial source were run on a proprietary LC/MS/MS platform. The retention time and the fragmentation spectrum received for Phe-Ser matched the time and spectrum of X-14208. Thus, using the above-described method, X-14208 was identified by testing only two candidate molecules.

Example 3

Previously unidentified biomarker X-14478 was identified using the following procedure.

The mass of the unknown X-14478 was determined in a LC/MS/MS run in positive ionization mode.

Following the GGM steps described above, a GGM network for X-14478 was obtained. Metabolites shown to have significant partial correlations to X-14478, are listed in Table 8.

TABLE 8

Metabolites having significant partial correlation with the unknown metabolite X-14478.

| Unknown: | Significant partial correlation to: | p-value |
|---|---|---|
| X-14478 | X-14208 | 4.67E−153 |
| | X-14205 | 4.22E−87 |
| | X-11805 | 3.95E−55 |
| | X-14450 | 4.67E−14 |
| | cysteineglutathionedisulfide | 5.67E−14 |
| | aspartylphenylalanine | 3.51E−10 |

FIG. 2 provides a GGM network showing the most significant direct and second neighbors of X-14478. Therein, the connectors connect significantly partially correlating metabolites. The connectors are weighted by the degree of significance (specifically, the lower the p-value of the correlation, the thicker the line).

For X-14478, checking for known reactions from metabolic databases did not provide additional connectors within a distance of two from the unknown. The majority of known metabolites occurring in the GGM of X-14478 are peptides, dipeptides, and amino acids.

The GGM network showed partial correlations of X-14478 with peptides, dipeptides and amino acids. It was hypothesized that X-14478 is a peptide, dipeptide or amino acid. Considering the mass of X-14478, the most probable candidate was the dipeptide Phe-Phe.

In order to experimentally confirm the hypothesis, the accurate mass of X-14478 was determined. For experimental validation, Phe-Phe from a commercial source was run on a proprietary LC/MS/MS platform. The retention time and the fragmentation spectrum received for Phe-Phe matched the time and spectrum of X-14478. Thus, using the above-described method, X-14478 was identified by testing only one candidate molecules.

Example 4

Previously unidentified biomarker X-11244 was identified using the following procedure.

The mass of the unknown X-11244 was determined in a LC/MS/MS run in negative ionization mode. The mass quantified for this unknown was 449.1.

Following the GGM steps described above, a GGM network for X-11244 was obtained. Metabolites shown to have significant partial correlations to X-11244, are listed in Table 9.

TABLE 9

Metabolites having significant partial correlation with the unknown metabolite X-11244.

| Unknown: | Significant partial correlation to: | p-value |
|---|---|---|
| X-11244 | X-11443 | 8.93E−113 |
| | X-11440 | 7.62E−93 |
| | dehydroisoandrosteronesulfateDHEAS | 7.47E−37 |
| | epiandrosteronesulfate | 6.66E−16 |
| | thromboxaneB2 | 1.12E−12 |
| | X-11470 | 4.12E−09 |

Figure 3:
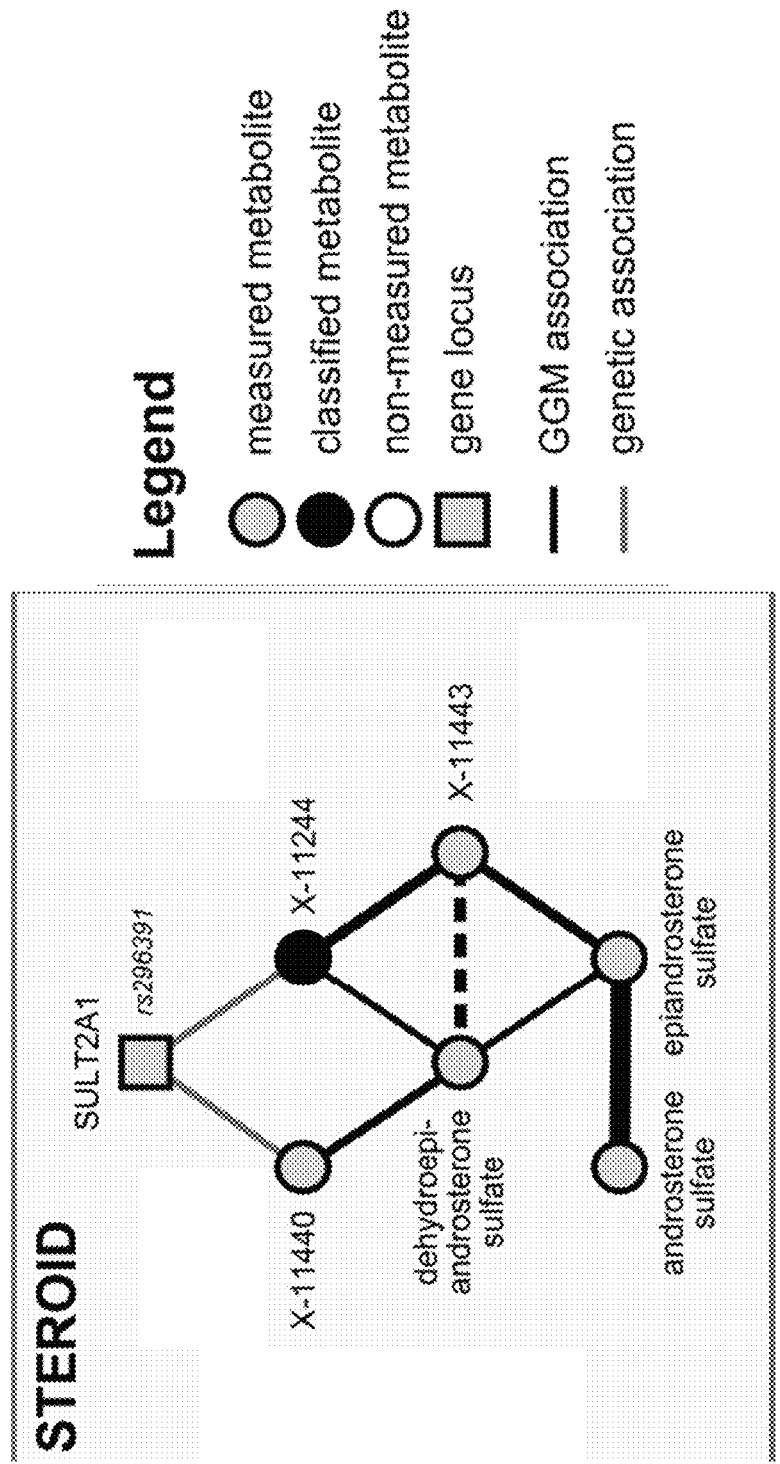
FIG. 3 is a graphical representation of an association network showing the most significant direct and second neighbors of X-11244. Solid lines denote positive partial correlations. Dashed lines indicate negative partial correlations.

FIG. 3 provides an illustration of the association network showing the biochemical edges from the GGM, genetic associations from the GWAS, and pathway annotations showing the most significant direct and second neighbors of X-11244. Therein, the connectors connect significantly partially correlating metabolites. The connectors are weighted by the degree of significance (specifically, the lower the p-value of the correlation, the thicker the line).

The majority of known metabolites occurring in the GGM of X-11244 are related to steroid-hormone compounds. Checking for known reactions from metabolic databases did not provide additional connectors within a distance of two from X-11244.

In the GWAS analysis, X-11244 was found to associate most significantly with a SNP in the gene encoding SULT2A1 which is a member of the sulfotransferase family 2A, dehydroepiandrosterone-preferring. Table 10 shows the most significant hit from the GWAS analysis for X-11244.

TABLE 10

Most significant hit in the GWAS for the unknown X-11244.

| Unknown | Best Assoc. SNP | Locus | Enzyme | p-value |
|---|---|---|---|---|
| X-11244 | rs296391 | SULT2A1; CRX | sulfotransferase family, cytosolic, 2A, dehydroepiandrosterone (DHEA)-preferring, member 1; cone-rod homeobox | 2.12E−26 |

When the results from the GGM and the GWAS were integrated, it appeared that besides X-11244, the sulfated steroids related to androsterone and the unknowns X-11440, and X-11443 were also significantly associated with SNPs in SULT2A1. It was hypothesized that X-11244 is a steroid sulfate related to androsterone.

In order to experimentally confirm the hypothesis, the accurate mass of X-11244 was determined. Its neutral mass of 450.13835 supported the formula $C_{19}H_{30}O_8S_2$. Using LC/MS/MS in negative ionization mode, the primary loss of a fragment with a nominal mass of 98 and the presence of an ion at 97 m/z were observed in the fragmentation spectrum of X-11244 which indicated the presence of at least one sulfate group in X-11244. For experimental validation, several disulfated androstenes from a commercial source were run on a proprietary LC/MS/MS platform. All demonstrated similar retention times and fragmentation spectra. Among the variants that were tested, 4-androsten-3β,17β-disulfate showed the best match to the retention time and fragmentation spectrum of X-11244. Given that other isomers are also possible, which cannot necessarily be chromatographically resolved, X-11244 was annotated more generically as androstene disulfate.

Example 5

Previously unidentified biomarker X-12441 was identified using the following procedure.

The mass of the unknown X-12441 was determined in a LC/MS/MS run in negative ionization mode. The mass quantified for this unknown was 319.2.

Following the GGM steps described above, a GGM network for X-12441 was obtained. Metabolites shown to have significant partial correlations to X-12441 are listed in Table 11.

TABLE 11

| Metabolites having significant partial correlation with the unknown metabolite X-12441. | | |
|---|---|---|
| Unknown: | Significant partial correlation to: | p-value |
| X-12441 | arachidonate204n6 | 1.52E−116 |
|  | @1arachidonoylglycerophosphocholine | 9.39E−13 |
|  | docosahexaenoateDHA226n3 | 2.74E−09 |
|  | X-10810 | 2.26E−07 |
|  | dihomolinolenate203n3orn6 | 6.48E−07 |

Figure 4:
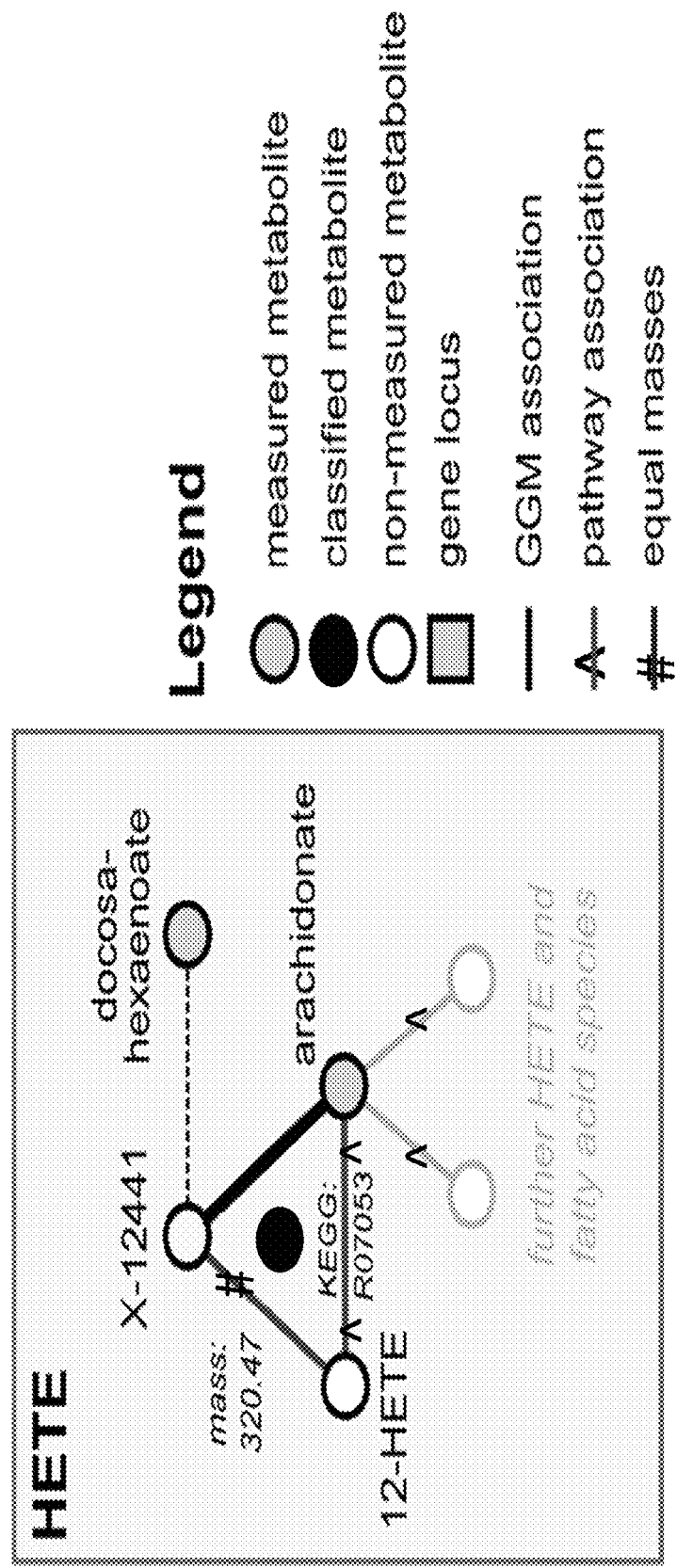
FIG. 4 is a graphical representation of an association network showing the most significant direct and second neighbors of X-12441. Solid lines denote positive partial correlations. Dashed lines indicate negative partial correlations.

FIG. 4 provides an association network showing the most significant direct and second neighbors of X-12441. Therein, the connectors connect significantly partially correlating metabolites. The connectors are weighted by the degree of significance (specifically, the lower the p-value of the correlation, the thicker the line). In FIG. 4, direct pathway interaction is shown between X-12441 and the known metabolite 12-HETE which has the same mass as X-12441.

In the GGM analysis, one GGM neighbor (arachidonate) was found. FIG. 4 shows that arachidonate has pathway connections to several lipid-related metabolites, including a variety of hydroxyl-arachidonate variants (HETEs). These HETE variants have the chemical formula $C_{20}H_{32}O_3$ and a molecular weight of 320.2351, which matched the mass of X-12441. When the results from the GGM, and pathway analysis were integrated, it was hypothesized that X-12441 was a species of HETE.

In order to experimentally confirm the hypothesis, the accurate mass of X-12441 was determined. Its neutral mass of 320.23430 supported the formula $C_{20}H_{32}O_3$, which also fits the hypothesis of a species of HETE, as this mass matches the chemical composition of HETE to a precision of +/−0.002 Da. For experimental validation, HETE isoforms 5, 8, 9, 11, 12 and 15 from a commercial source were run on a proprietary LC/MS/MS platform. The retention time and the fragmentation spectrum of the 12-HETE isoform matched the time and spectrum of X-12441. Thus, using the above-described method, X-12441 was identified by testing six HETE isoforms and was identified as 12-HETE.

Example 6

Previously unidentified biomarker X-11421 was identified using the following procedure.

The mass of the unknown X-11421 was determined in a LC/MS/MS run in positive ionization mode.

Following the GGM steps described above, a GGM network for X-11421 was obtained. Metabolites shown to have significant partial correlations to X-11421 are listed in Table 12.

TABLE 12

| Metabolites having significant partial correlation with the unknown metabolite X-11421. | | |
|---|---|---|
| Unknown: | Significant partial correlation to: | p-value |
| X-11421 | X-13435 | 9.93E−56 |
|  | linoleate182n6 | 1.55E−45 |
|  | octanoylcarnitine | 1.05E−40 |
|  | hexanoylcarnitine | 1.00E−23 |

Figure 5:
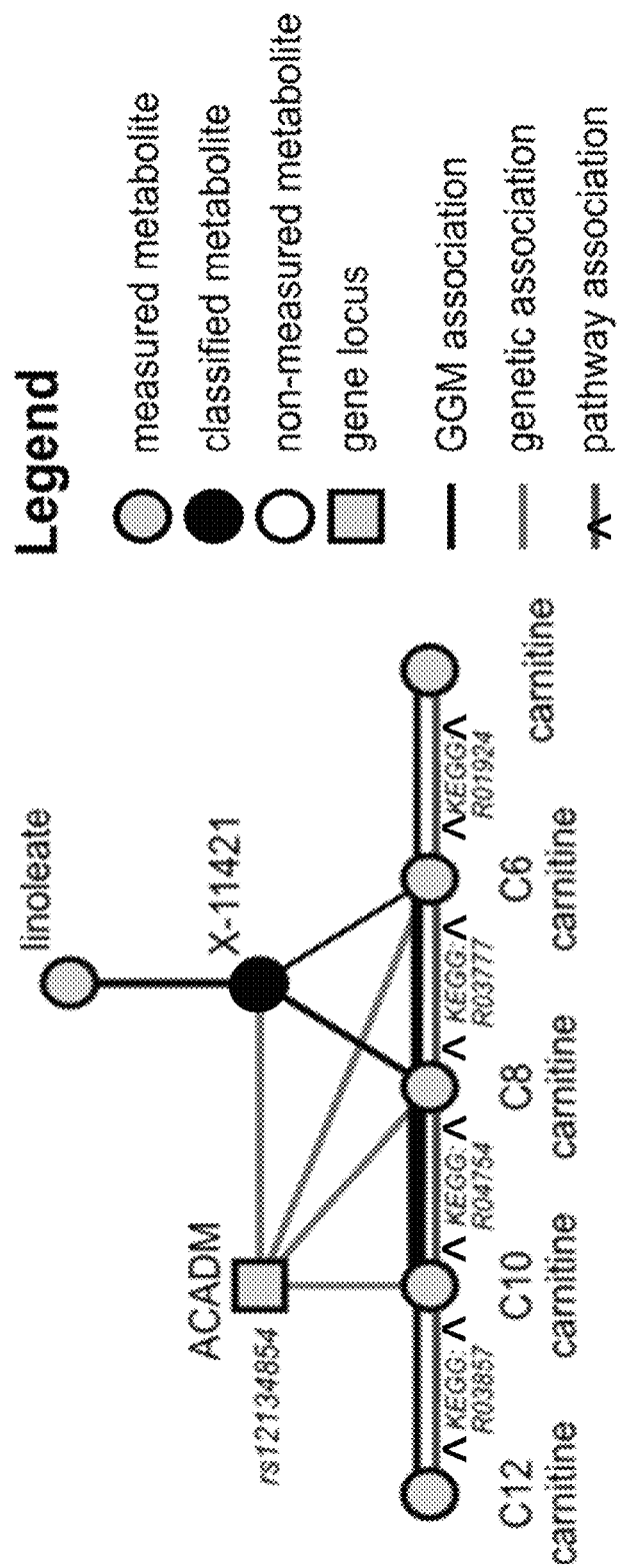
FIG. 5 is a graphical representation of an association network showing the most significant direct and second neighbors of X-11421. Solid lines denote positive partial correlations. Dashed lines indicate negative partial correlations.

FIG. 5 provides an association network showing the most significant direct and second neighbors of X-11421. This network incorporates GGM, GWAS and pathway associations. The connectors connect significantly partially correlating metabolites. The connectors are weighted by the degree of significance (specifically, the lower the p-value of the correlation, the thicker the line).

For X-11421, checking for known reactions from metabolic databases revealed carnitine species as additional connectors within a distance of two from the unknown. The majority of known metabolites occurring in the GGM of X-11421 are carnitine species.

In the GWAS analysis, X-11421 was found to associate most significantly with a SNP in the gene encoding the acyl-coenzyme A dehydrogenase (ACAD) for medium-chain length fatty acyl residues (ACADM). Table 13 shows the most significant hit from the GWAS analysis for X-11421. When the results from the GGM, GWAS and pathway analyses were integrated, it was hypothesized that X-11421 is a medium-chain length carnitine.

TABLE 13

| Most significant hit in the GWAS for the unknown X-11421. | | | | |
|---|---|---|---|---|
| Unknown | Best Assoc. SNP | Locus | Enzyme | p-value |
| X-11421 | rs12134854 | ACADM | acyl-CoA dehydrogenase, C-4 to C-12 straight chain | 1.90E−27 |

To experimentally confirm the hypothesis generated from the GGM, GWAS and pathway analyses, the accurate mass of X-11421 was determined. The LC/MS/MS analysis experimentally validated the hypothesis since the results showed that the retention time and fragmentation spectrum of X-11421 matched the retention time and fragmentation spectrum of cis-4-decenoyl-carnitine. Thus, using the above-described method, X-11421 was identified as cis-4-decenoyl-carnitine which is a carnitine with 10 carbon atoms and an ω-6 double bond.

Example 7

Previously unidentified biomarker X-13431 was identified using the following procedure.

The mass of the unknown X-13431 was determined in a LC/MS/MS run in positive ionization mode. The mass quantified for this unknown was 302.2.

Following the GGM steps described above, a GGM network for X-13431 was obtained. Metabolites shown to have significant partial correlations to X-13431 are listed in Table 14.

TABLE 14

Metabolites having significant partial correlation with the unknown metabolite X-13431.

| Unknown: | Significant partial correlation to: | p-value |
|---|---|---|
| X-13431 | @10undecenoate111n1 | 1.82E-14 |
| | @2methylbutyroylcarnitine | 6.68E-13 |
| | X-12442 | 5.43E-12 |
| | @1palmitoleoylglycerophosphocholine | 2.75E-07 |

Figure 6:
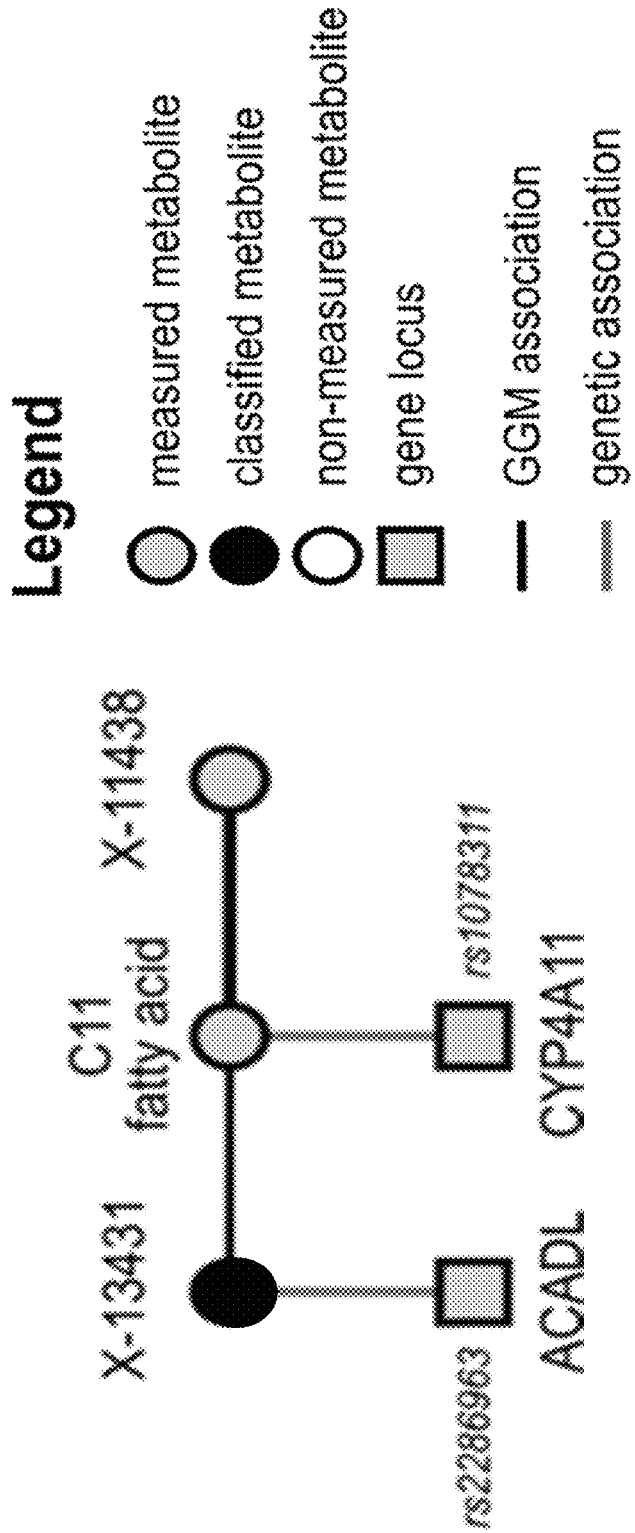
FIG. 6 is a graphical representation of an association network showing the most significant direct and second neighbors of X-13431. Solid lines denote positive partial correlations. Dashed lines indicate negative partial correlations.

FIG. 6 provides an association network showing the most significant direct and second neighbors of X-13431. This network incorporates GGM and GWAS associations. The connectors connect significantly partially correlating metabolites. The connectors are weighted by the degree of significance (specifically, the lower the p-value of the correlation, the thicker the line).

For X-13431, checking for known reactions from metabolic databases did not provide additional connectors within a distance of two from the unknown. The GGM of X-13431 shows an association with a C11 fatty acid.

In the GWA analysis, X-13431 was found to associate most significantly with a SNP in the gene encoding the acyl-coenzyme A dehydrogenase (ACAD) for long-chain length fatty acyl residues (ACADL). ACADL has been shown to alter C9 carnitines. Table 15 shows the most significant hit from the GWAS analysis for X-13431. When the results from the GGM and GWAS analyses were integrated, it was hypothesized that X-13431 is a C9 carnitine.

TABLE 15

Most significant hit in the GWAS for the unknown X-13431.

| Unknown | Best Assoc. SNP | Locus | Enzyme | p-value |
|---|---|---|---|---|
| X-13431 | rs2286963 | ACADL | acyl-CoA dehydrogenase, long chain | 2.68E-33 |

In order to experimentally confirm the hypothesis, the accurate mass of X-13431 was determined. Its neutral mass 301.22476 supported the formula $C_{16}H_{31}NO_4$, which also is consistent with the hypothesis of a C9 carnitine. Exact mass, fragmentation pattern and chromatographic retention time supported the identification of X-13431 as nonanoyl carnitine. Thus, using the above-described method, X-13431 was identified as nonanoyl carnitine.

Example 8

Previously unidentified biomarker X-11793 was identified using the following procedure.

The mass of the unknown X-11793 was determined in a LC/MS/MS run in positive ionization mode. The mass quantified for this unknown was 601.26587.

Following the GGM steps described above, a GGM network for X-11793 was obtained. Metabolites shown to have significant partial correlations to X-11793 are listed in Table 16.

TABLE 16

Metabolites having significant partial correlation with the unknown metabolite X-11793.

| Unknown: | Significant partial correlation to: | p-value |
|---|---|---|
| X-11793 | bilirubinEE | 8.57E-108 |

Figure 7:
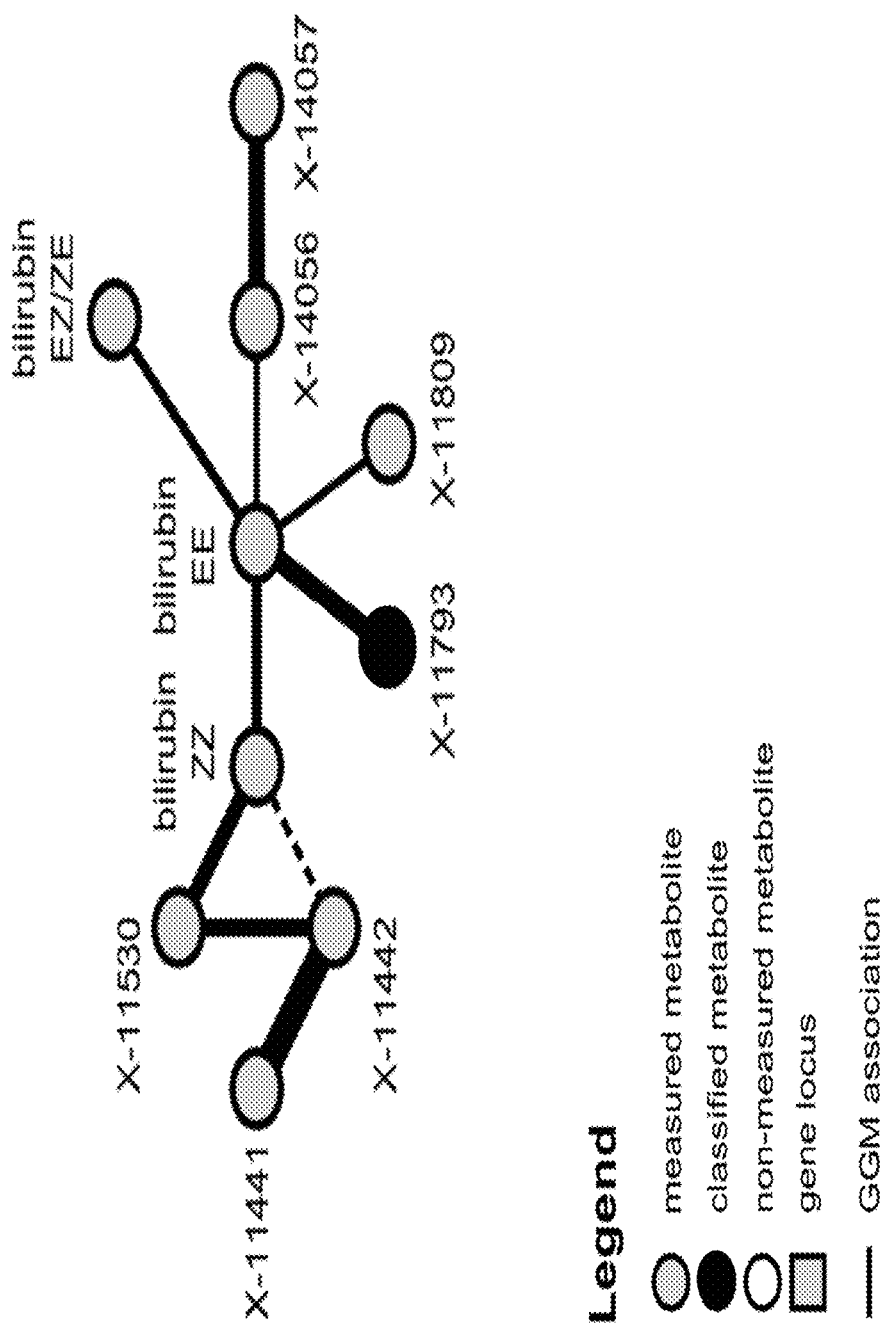
FIG. 7 is a graphical representation of an association network showing the most significant direct and second neighbors of X-11793. Solid lines denote positive partial correlations. Dashed lines indicate negative partial correlations.

FIG. 7 provides an association network showing the most significant direct and second neighbors of X-11793. This network incorporates GGM and GWAS associations. The connectors connect significantly partially correlating metabolites. The connectors are weighted by the degree of significance (specifically, the lower the p-value of the correlation, the thicker the line).

For X-11793, checking for known reactions from metabolic databases did not provide additional connectors within a distance of two from the unknown. The GGM of X-11793 shows an association with three bilirubin steroisoforms.

In the GWAS analysis, X-11793 was found to associate most significantly with a SNP in the gene encoding the UDP glucuronosyltransferase 1 family, polypeptide A. Table 17 shows the most significant hit from the GWAS analysis for X-11793. When the results from the GGM and GWAS analyses were integrated, it was hypothesized that X-11793 is an oxidized bilirubin variant.

TABLE 17

Most significant hit in the GWAS for the unknown X-11793.

| Unknown | Best Assoc. SNP | Locus | Enzyme | p-value |
|---|---|---|---|---|
| X-11793 | rs887829 | UGT1A | UDP glucuronosyl-transferase 1 family, polypeptide A | 2.59E-26 |

In order to experimentally confirm the hypothesis, the accurate mass of X-11793 was determined. Its neutral mass 600.25859 supported the formula $C_{33}H_{36}N_4O_7$, which also is consistent with the hypothesis of an oxidized bilirubin variant. Exact mass, fragmentation pattern and chromatographic retention time supported to identification of X-11793 as an oxidized bilirubin variant. Thus, using the above-described method, X-11793 was identified as an oxidized bilirubin variant.

Example 9

Previously unidentified biomarker X-11593 was identified using the following procedure.

The mass of the unknown X-11593 was determined in a LC/MS/MS run in negative ionization mode. The mass quantified for this unknown was 189.2.

Figure 8:
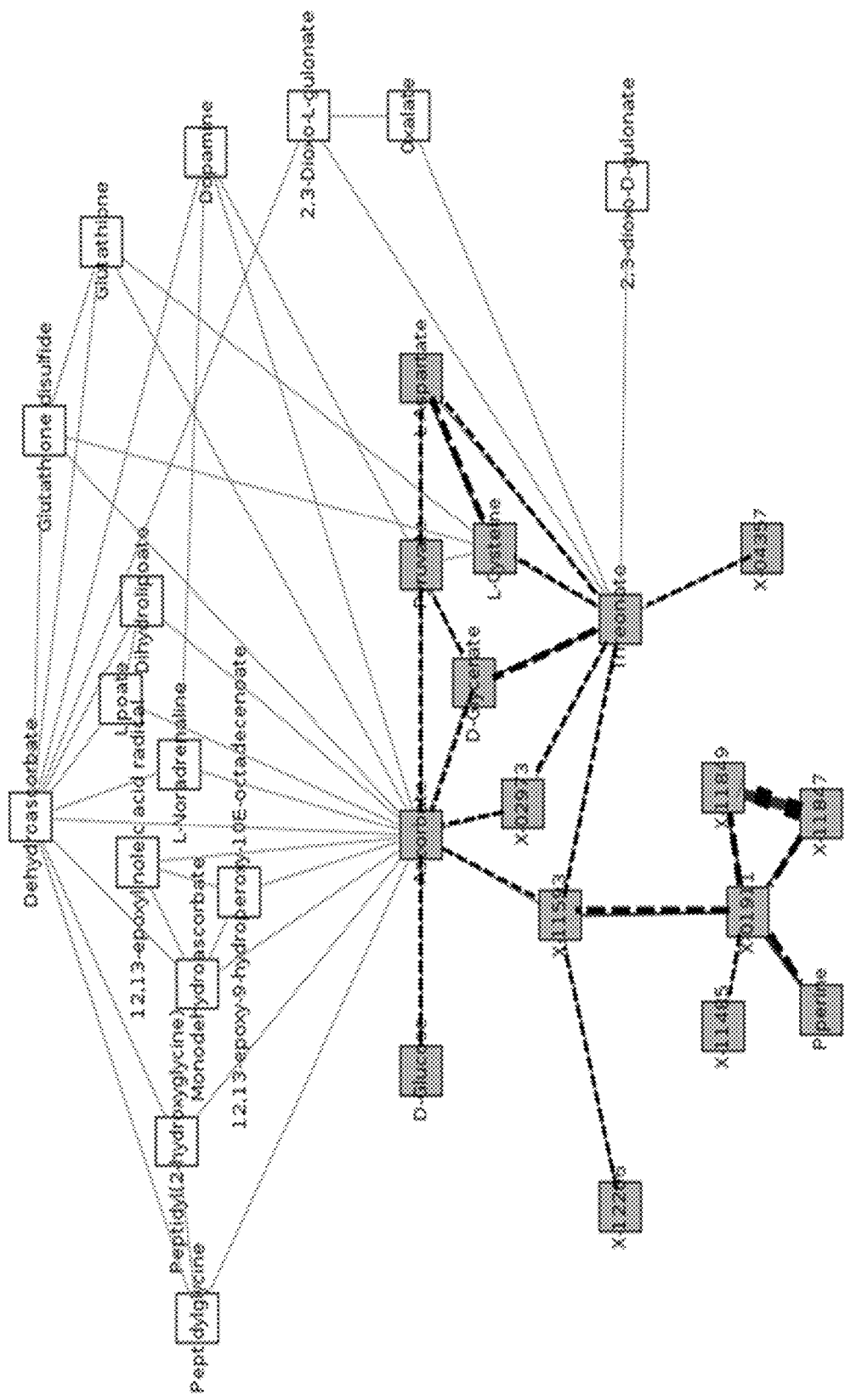
FIG. 8 is a graphical representation of a GGM network showing the most significant direct and second neighbors of X-11593.

The GGM for X-11593, including its direct and second neighbors, is shown in FIG. 8. In FIG. 8, only connectors having correlation with p-values below 0.001/(n(n−1)/2) are shown. All metabolites with significant partial correlations to X-11593, at a significance level of 0.05, are listed in Table 18. In FIG. 8, broken line (dashed) connectors denote significant partial correlations between the connected metabolites while solid line (gray) connectors represent connections via a known biochemical reaction as provided by metabolic databases such as KEGG. The lines are weighted by p-value, the lower the p-value, the thicker the line. Both known metabolites directly associated with X-11593 belong to the ascorbate degradation pathway.

TABLE 18

Metabolites having significant partial correlation with the unknown metabolite X-11593.

| Unknown: | Significant partial correlation to: | p-value |
|---|---|---|
| X-11593 | X-01911 | 8.00E−38 |
|  | ascorbate | 6.59E−20 |
|  | threonate | 6.92E−20 |
|  | X-12206 | 1.98E−11 |
|  | 1,5-anhydroglucitol (1,5-AG) | 1.26E−07 |
|  | C-glycosyltryptophan | 6.80E−07 |

In the GWAS analysis, significant associations of X-11593 with SNPs in the gene encoding catechol-O-methyltransferase (COMT) were found. Table 19 shows the most significant hit from the GWAS analysis for X-11593. COMT is an enzyme relevant for the inactivation and degradation of many drugs. COMT O-methylates molecules with catechol like structures.

TABLE 19

Most significant hit in the GWAS for the unknown X-11593.

| Unknown | Best Assoc. SNP | Locus | Enzyme | p-value |
|---|---|---|---|---|
| X-11593 | rs4680 | COMT | catechol-O-methyltransferase | 1.13E−48 |

The constraints for X-11593 given by the GGM shown in FIG. 8 and given by the GWAS analysis were combined. According to the GWAS, X-11593 was probably a substrate or a product of O-methylation. The mass differences to the known metabolites neighboring X-11593, namely ascorbate and threonate, was determined. While the mass difference of X-11593 and threonate is 54, X-11593 and ascorbate show a mass difference of 14, which corresponds to the addition of a methyl moiety. These observations made O-methylated ascorbate derivatives good candidates for X-11593.

From an experimental perspective, this hypothesis was supported by the accurate neutral mass 190.04787 determined for X-11593. Based on the accurate mass, the molecular formula for X-11593 was determined to be $C_7H_{10}O_6$. In ChemSpider, 93 molecules were described for this formula. Out of the 93 molecules, three molecules represent O-methylated ascorbates. Their structures are shown in Formulas I, II, and III below. Two of the three molecules are methylated at one of the hydroxyl moieties of the 5-ring. The double bond within the 5-ring with its two hydroxyl moieties could "mimic" the corresponding planar substructure in catechol, on which catechol-o-methyltransferase (COMT) is usually working. As such, the molecules of Formulas I and II are more probable candidates for X-11593. Experimentally, the retention time of X-11593 showed a slight shift compared to the time for ascorbate. This shift matches the shift expected for adding a methyl group. Moreover, the primary fragment loss for X-11593 is 60, which is the same as that for ascorbate. The mass loss of 15, also seen for X-11593, is typical for phenols substituted with a —OH and —OCH₃. Thus, it was hypothesized that X-11593 is 2-O-methyl ascorbic acid.

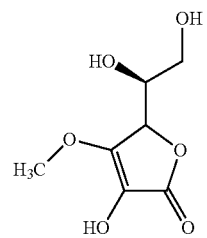

I

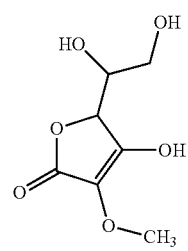

II

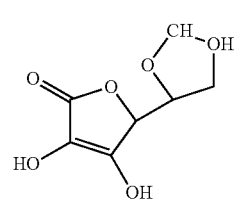

III

Candidate Molecules for X-11593

TABLE 2

| UNKNOWN | ASSOCIATING SNP | PVAL_SNP |
|---|---|---|
| X01911 | rs4680 | 5.80E−11 |
| X01911 | rs165656 | 3.65E−10 |
| X01911 | rs176533 | 6.39E−07 |
| X01911 | rs4633 | 3.95E−08 |
| X02249 | rs867212 | 1.502E−06 |
| X02269 | rs6583967 | 4.84E−07 |
| X02973 | rs12652460 | 2.164E−06 |
| X03003 | rs10879287 | 6.13E−07 |
| X03056 | rs4240520 | 3.03E−08 |
| X03088 | rs7329126 | 1.322E−06 |
| X03090 | rs4952293 | 9.08E−07 |
| X03094 | rs3741298 | 1.49E−09 |
| X04357 | rs1953661 | 3.804E−06 |
| X04494 | rs9365108 | 4.653E−06 |
| X04495 | rs7634246 | 1.246E−06 |
| X04498 | rs3848141 | 2.59E−07 |
| X04499 | rs17076477 | 1.15E−07 |
| X04500 | rs2920861 | 1.081E−06 |
| X04515 | rs7785988 | 1.082E−06 |
| X05426 | rs1881514 | 1.67E−07 |
| X05491 | rs16823855 | 6.43E−07 |
| X05907 | rs1635181 | 3.764E−06 |
| X06126 | rs353807 | 8.06E−07 |
| X06226 | rs12413935 | 4.09E−11 |
| X06227 | rs1695945 | 6.75E−07 |
| X06246 | rs2219008 | 5.56E−07 |
| X06267 | rs17138748 | 4.229E−06 |
| X06307 | rs9316180 | 4.93E−09 |
| X06350 | rs12028243 | 6.31E−07 |
| X06351 | rs13097461 | 9.91E−07 |
| X07765 | rs4687417 | 9.67E−07 |
| X08402 | rs4902250 | 1.18E−09 |
| X08766 | rs11621845 | 1.193E−06 |
| X08988 | rs1398806 | 9.03E−07 |
| X09026 | rs9320134 | 1.32E−07 |
| X09108 | rs10972022 | 1.514E−06 |
| X09706 | rs803422 | 3.64E−07 |
| X09789 | rs2588976 | 1.49E−07 |
| X10346 | rs6432834 | 1.764E−06 |

TABLE 2-continued

| UNKNOWN | ASSOCIATING SNP | PVAL_SNP |
|---|---|---|
| X10395 | rs10497458 | 2.54E−08 |
| X10419 | rs10260816 | 2.78E−06 |
| X10429 | rs6767775 | 4.028E−06 |
| X10500 | rs16946189 | 1.76E−06 |
| X10506 | rs1284066 | 9.82E−07 |
| X10510 | rs11856508 | 2.85E−07 |
| X10675 | rs2279812 | 4.77E−07 |
| X10810 | rs9610927 | 1.122E−06 |
| X11204 | rs1545358 | 1.234E−05 |
| X11244 | rs296391 | 2.12E−26 |
| X11244 | rs17272617 | 5.87E−13 |
| X11244 | rs2910400 | 4.38E−07 |
| X11244 | rs2932766 | 6.42E−09 |
| X11244 | rs2972515 | 3.14E−07 |
| X11244 | rs3745752 | 2.10E−10 |
| X11244 | rs4427918 | 5.77E−07 |
| X11247 | rs2807872 | 7.14E−08 |
| X11255 | rs8179972 | 1.694E−06 |
| X11261 | rs1247499 | 8.16E−07 |
| X11299 | rs671938 | 2.372E−06 |
| X11315 | rs7782739 | 1.325E−06 |
| X11317 | rs4575635 | 8.02E−08 |
| X11319 | rs11118895 | 2.90E−07 |
| X11327 | rs7129081 | 7.47E−07 |
| X11334 | rs16833988 | 1.725E−06 |
| X11374 | rs457075 | 3.39E−07 |
| X11381 | rs11106542 | 1.355E−06 |
| X11412 | rs359980 | 3.19E−07 |
| X11421 | rs12134854 | 1.90E−27 |
| X11421 | rs1001160 | 7.58E−11 |
| X11421 | rs10873788 | 2.05E−18 |
| X11421 | rs11161510 | 3.86E−25 |
| X11421 | rs11161511 | 2.20E−25 |
| X11421 | rs11161620 | 2.71E−19 |
| X11421 | rs11163904 | 1.16E−09 |
| X11421 | rs11163924 | 2.62E−25 |
| X11421 | rs1146579 | 2.28E−22 |
| X11421 | rs11579752 | 2.03E−09 |
| X11421 | rs1159215 | 1.20E−10 |
| X11421 | rs12090849 | 1.00E−18 |
| X11421 | rs12123977 | 8.67E−26 |
| X11421 | rs12131344 | 9.98E−11 |
| X11421 | rs12140121 | 1.13E−17 |
| X11421 | rs1250876 | 5.65E−14 |
| X11421 | rs1251079 | 1.61E−13 |
| X11421 | rs1251551 | 2.25E−12 |
| X11421 | rs1251584 | 5.87E−10 |
| X11421 | rs1303870 | 9.88E−13 |
| X11421 | rs1498311 | 1.35E−10 |
| X11421 | rs1689271 | 9.29E−12 |
| X11421 | rs1694419 | 1.61E−16 |
| X11421 | rs17097780 | 3.05E−08 |
| X11421 | rs17647178 | 2.02E−11 |
| X11421 | rs17650138 | 3.97E−16 |
| X11421 | rs1770887 | 1.36E−15 |
| X11421 | rs1796812 | 1.62E−12 |
| X11421 | rs211718 | 6.38E−27 |
| X11421 | rs2792664 | 3.51E−11 |
| X11421 | rs3818855 | 1.16E−19 |
| X11421 | rs5745347 | 4.19E−11 |
| X11421 | rs6699682 | 8.66E−19 |
| X11421 | rs7516477 | 1.25E−13 |
| X11421 | rs7519526 | 1.51E−11 |
| X11421 | rs7547056 | 9.14E−15 |
| X11421 | rs8396 | 2.01E−07 |
| X11422 | rs2406278 | 2.70E−07 |
| X11423 | rs6429032 | 1.43E−06 |
| X11437 | rs7779508 | 2.761E−06 |
| X11438 | rs174456 | 3.052E−06 |
| X11440 | rs296391 | 1.69E−43 |
| X11440 | rs17272617 | 9.63E−24 |
| X11440 | rs2910400 | 1.55E−11 |
| X11440 | rs2932766 | 5.51E−14 |
| X11440 | rs2972515 | 1.60E−12 |
| X11440 | rs3745752 | 1.08E−15 |
| X11440 | rs4427918 | 2.68E−09 |
| X11441 | rs6742078 | 5.59E−30 |
| X11441 | rs887829 | 2.79E−29 |
| X11441 | rs10179091 | 2.27E−18 |
| X11441 | rs10197460 | 2.09E−19 |
| X11441 | rs10203853 | 4.62E−08 |
| X11441 | rs11695484 | 8.25E−23 |
| X11441 | rs11891311 | 7.16E−17 |
| X11441 | rs2602380 | 2.24E−07 |
| X11441 | rs2741021 | 1.23E−14 |
| X11441 | rs2741023 | 1.68E−09 |
| X11441 | rs2741045 | 3.61E−23 |
| X11441 | rs3755319 | 3.31E−20 |
| X11441 | rs3806596 | 1.35E−21 |
| X11441 | rs3806597 | 9.58E−22 |
| X11441 | rs4294999 | 7.55E−21 |
| X11441 | rs4663965 | 1.21E−22 |
| X11441 | rs6714634 | 1.33E−22 |
| X11441 | rs6715325 | 2.07E−14 |
| X11441 | rs6736508 | 1.91E−18 |
| X11441 | rs6744284 | 4.49E−23 |
| X11441 | rs6753320 | 9.87E−18 |
| X11441 | rs6759892 | 2.74E−18 |
| X11441 | rs6761246 | 8.01E−07 |
| X11441 | rs7563561 | 5.68E−18 |
| X11441 | rs7564935 | 3.93E−19 |
| X11441 | rs7608175 | 6.89E−18 |
| X11442 | rs6742078 | 1.19E−25 |
| X11442 | rs887829 | 2.18E−25 |
| X11442 | rs10179091 | 8.51E−18 |
| X11442 | rs10197460 | 4.41E−16 |
| X11442 | rs10203853 | 3.78E−08 |
| X11442 | rs11695484 | 2.27E−21 |
| X11442 | rs11891311 | 3.83E−16 |
| X11442 | rs2741021 | 3.39E−12 |
| X11442 | rs2741023 | 6.41E−08 |
| X11442 | rs2741045 | 2.68E−19 |
| X11442 | rs3755319 | 1.58E−19 |
| X11442 | rs3806596 | 8.71E−21 |
| X11442 | rs3806597 | 8.89E−21 |
| X11442 | rs4294999 | 8.97E−20 |
| X11442 | rs4663965 | 4.82E−22 |
| X11442 | rs6714634 | 2.18E−21 |
| X11442 | rs6715325 | 1.37E−15 |
| X11442 | rs6736508 | 1.77E−15 |
| X11442 | rs6744284 | 1.20E−20 |
| X11442 | rs6753320 | 1.99E−14 |
| X11442 | rs6759892 | 1.76E−15 |
| X11442 | rs7563561 | 8.52E−15 |
| X11442 | rs7564935 | 1.15E−18 |
| X11442 | rs7608175 | 7.05E−15 |
| X11443 | rs16845476 | 4.651E−06 |
| X11444 | rs12466713 | 3.295E−06 |
| X11445 | rs296391 | 7.91E−07 |
| X11445 | rs13358334 | 2.36E−12 |
| X11445 | rs4149056 | 5.26E−08 |
| X11445 | rs4149081 | 8.46E−08 |
| X11445 | rs10461715 | 4.34E−11 |
| X11445 | rs11045879 | 1.69E−07 |
| X11445 | rs11746242 | 2.09E−07 |
| X11445 | rs2039623 | 9.49E−07 |
| X11445 | rs3756669 | 4.32E−12 |
| X11445 | rs700176 | 4.63E−07 |
| X11445 | rs7715372 | 2.10E−12 |
| X11445 | rs852238 | 3.66E−08 |
| X11450 | rs17325782 | 1.745E−06 |
| X11452 | rs253444 | 1.837E−06 |
| X11469 | rs4712963 | 5.57E−08 |
| X11470 | rs879154 | 4.09E−07 |
| X11478 | rs16946426 | 4.40E−07 |
| X11483 | rs10505816 | 5.91E−08 |
| X11485 | rs17361212 | 5.50E−08 |
| X11491 | rs4149056 | 7.76E−08 |
| X11497 | rs17265949 | 1.60E−07 |
| X11521 | rs6082408 | 5.39E−07 |
| X11529 | rs4149056 | 3.28E−81 |
| X11529 | rs4149081 | 1.93E−71 |
| X11529 | rs10841753 | 1.30E−11 |
| X11529 | rs10841791 | 4.70E−08 |
| X11529 | rs11045818 | 7.26E−12 |
| X11529 | rs11045819 | 3.44E−11 |

TABLE 2-continued

| UNKNOWN | ASSOCIATING SNP | PVAL_SNP |
|---|---|---|
| X11529 | rs11045821 | 4.57E−13 |
| X11529 | rs11045825 | 1.36E−12 |
| X11529 | rs11045872 | 6.72E−11 |
| X11529 | rs11045879 | 2.58E−72 |
| X11529 | rs11045907 | 5.73E−12 |
| X11529 | rs11045908 | 2.09E−11 |
| X11529 | rs11045913 | 1.58E−19 |
| X11529 | rs11045953 | 2.17E−07 |
| X11529 | rs12372067 | 3.29E−18 |
| X11529 | rs12372111 | 5.22E−18 |
| X11529 | rs12812279 | 6.55E−13 |
| X11529 | rs1463565 | 8.81E−13 |
| X11529 | rs16923647 | 8.73E−52 |
| X11529 | rs2007379 | 1.66E−07 |
| X11529 | rs2169969 | 5.65E−12 |
| X11529 | rs2196019 | 3.70E−07 |
| X11529 | rs2199766 | 7.47E−07 |
| X11529 | rs2291075 | 5.84E−21 |
| X11529 | rs2291076 | 2.88E−14 |
| X11529 | rs2417963 | 2.10E−15 |
| X11529 | rs2900476 | 6.55E−49 |
| X11529 | rs4148984 | 4.24E−07 |
| X11529 | rs4148987 | 2.62E−07 |
| X11529 | rs4148988 | 4.53E−08 |
| X11529 | rs4149035 | 3.31E−08 |
| X11529 | rs4149057 | 1.52E−37 |
| X11529 | rs4149058 | 1.88E−54 |
| X11529 | rs4149069 | 2.06E−15 |
| X11529 | rs4149076 | 2.31E−22 |
| X11529 | rs7313671 | 8.1E−08 |
| X11529 | rs7965567 | 1.04E−07 |
| X11529 | rs7966613 | 8.95E−20 |
| X11529 | rs7967303 | 4.47E−07 |
| X11529 | rs7975631 | 2.32E−07 |
| X11529 | rs852549 | 2.87E−07 |
| X11529 | rs919840 | 8.13E−07 |
| X11529 | rs999278 | 1.05E−13 |
| X11530 | rs6742078 | 2.12E−38 |
| X11530 | rs887829 | 2.30E−38 |
| X11530 | rs10179091 | 3.43E−23 |
| X11530 | rs10197460 | 3.15E−21 |
| X11530 | rs10203853 | 3.21E−10 |
| X11530 | rs10209214 | 2.33E−07 |
| X11530 | rs11695484 | 8.23E−33 |
| X11530 | rs11891311 | 2.51E−23 |
| X11530 | rs17864661 | 6.67E−07 |
| X11530 | rs2602379 | 4.21E−08 |
| X11530 | rs2602380 | 3.62E−08 |
| X11530 | rs2741021 | 1.58E−16 |
| X11530 | rs2741023 | 3.64E−10 |
| X11530 | rs2741045 | 4.14E−25 |
| X11530 | rs3755319 | 3.71E−27 |
| X11530 | rs3806596 | 1.78E−28 |
| X11530 | rs3806597 | 5.61E−29 |
| X11530 | rs4148328 | 1.05E−08 |
| X11530 | rs4294999 | 3.20E−27 |
| X11530 | rs4663965 | 1.86E−27 |
| X11530 | rs6714634 | 9.08E−32 |
| X11530 | rs6715325 | 1.74E−21 |
| X11530 | rs6736508 | 5.10E−19 |
| X11530 | rs6744284 | 2.02E−31 |
| X11530 | rs6753320 | 3.05E−17 |
| X11530 | rs6754100 | 4.35E−09 |
| X11530 | rs6759892 | 8.45E−19 |
| X11530 | rs6761246 | 3.97E−09 |
| X11530 | rs7563561 | 1.07E−19 |
| X11530 | rs7564935 | 4.07E−24 |
| X11530 | rs7587916 | 2.64E−09 |
| X11530 | rs7608175 | 1.79E−19 |
| X11537 | rs1529294 | 8.715E−06 |
| X11538 | rs4149056 | 1.35E−37 |
| X11538 | rs4149081 | 1.54E−34 |
| X11538 | rs10841753 | 2.01E−23 |
| X11538 | rs10841791 | 1.93E−12 |
| X11538 | rs11045512 | 2.53E−09 |
| X11538 | rs11045521 | 2.31E−09 |
| X11538 | rs11045598 | 4.60E−12 |
| X11538 | rs11045611 | 3.81E−12 |
| X11538 | rs11045721 | 6.32E−11 |
| X11538 | rs11045767 | 6.50E−15 |
| X11538 | rs11045773 | 2.87E−15 |
| X11538 | rs11045776 | 4.64E−11 |
| X11538 | rs11045787 | 3.60E−16 |
| X11538 | rs11045818 | 1.94E−28 |
| X11538 | rs11045819 | 5.99E−28 |
| X11538 | rs11045821 | 8.73E−28 |
| X11538 | rs11045825 | 2.02E−27 |
| X11538 | rs11045872 | 7.95E−25 |
| X11538 | rs11045879 | 1.06E−34 |
| X11538 | rs11045907 | 2.03E−20 |
| X11538 | rs11045908 | 9.50E−19 |
| X11538 | rs11045913 | 6.03E−20 |
| X11538 | rs11045953 | 2.09E−12 |
| X11538 | rs12366506 | 4.50E−12 |
| X11538 | rs12370666 | 1.53E−14 |
| X11538 | rs12370697 | 2.17E−14 |
| X11538 | rs12431442 | 2.87E−07 |
| X11538 | rs12812279 | 2.73E−25 |
| X11538 | rs16923647 | 1.32E−26 |
| X11538 | rs17328763 | 2.08E−16 |
| X11538 | rs2007379 | 4.40E−07 |
| X11538 | rs2169969 | 1.22E−25 |
| X11538 | rs2199766 | 1.67E−20 |
| X11538 | rs2857468 | 1.53E−09 |
| X11538 | rs2900476 | 1.05E−16 |
| X11538 | rs3794319 | 3.18E−10 |
| X11538 | rs4148984 | 5.56E−12 |
| X11538 | rs4148987 | 2.55E−10 |
| X11538 | rs4148988 | 1.80E−12 |
| X11538 | rs4149057 | 1.20E−14 |
| X11538 | rs4149058 | 7.42E−18 |
| X11538 | rs718545 | 8.84E−07 |
| X11538 | rs7313671 | 1.10E−12 |
| X11538 | rs7962263 | 3.66E−11 |
| X11538 | rs7965567 | 3.95E−07 |
| X11538 | rs7967303 | 1.78E−11 |
| X11538 | rs919840 | 4.67E−07 |
| X11540 | rs10798980 | 1.642E−06 |
| X11546 | rs17700286 | 2.58E−06 |
| X11550 | rs894282 | 3.692E−06 |
| X11552 | rs12512174 | 1.062E−06 |
| X11568 | rs10449290 | 3.549E−06 |
| X11593 | rs4680 | 1.13E−48 |
| X11593 | rs1034564 | 5.36E−08 |
| X11593 | rs1034565 | 3.2E−08 |
| X11593 | rs1110478 | 4.80E−08 |
| X11593 | rs1375450 | 1.68E−07 |
| X11593 | rs1544325 | 6.70E−23 |
| X11593 | rs1640299 | 2.96E−13 |
| X11593 | rs165656 | 1.16E−46 |
| X11593 | rs16982844 | 1.92E−08 |
| X11593 | rs17119998 | 1.62E−07 |
| X11593 | rs17120009 | 2.41E−07 |
| X11593 | rs175165 | 2.17E−11 |
| X11593 | rs175197 | 2.28E−07 |
| X11593 | rs175199 | 8.76E−08 |
| X11593 | rs175200 | 1.74E−08 |
| X11593 | rs2073746 | 1.53E−12 |
| X11593 | rs2266943 | 7.17E−07 |
| X11593 | rs385773 | 7.78E−09 |
| X11593 | rs397701 | 8.14E−07 |
| X11593 | rs404060 | 8.69E−07 |
| X11593 | rs4633 | 9.74E−35 |
| X11593 | rs4646312 | 3.79E−22 |
| X11593 | rs4646316 | 3.14E−08 |
| X11593 | rs5748489 | 1.05E−19 |
| X11593 | rs5993875 | 2.90E−14 |
| X11593 | rs5993883 | 4.85E−16 |
| X11593 | rs8185002 | 2.58E−09 |
| X11593 | rs885980 | 5.18E−09 |
| X11593 | rs9332377 | 3.24E−07 |
| X11593 | rs9605063 | 5.38E−07 |
| X11593 | rs9606240 | 6.32E−10 |
| X11786 | rs7251736 | 3.11E−07 |
| X11787 | rs6710438 | 2.95E−37 |
| X11787 | rs7598396 | 1.66E−35 |

TABLE 2-continued

| UNKNOWN | ASSOCIATING SNP | PVAL_SNP |
|---|---|---|
| X11787 | rs6753344 | 7.28E−36 |
| X11787 | rs10190002 | 8.81E−21 |
| X11787 | rs10193032 | 9.46E−13 |
| X11787 | rs10496190 | 1.75E−21 |
| X11787 | rs1052161 | 4.01E−21 |
| X11787 | rs1052162 | 1.94E−34 |
| X11787 | rs1083922 | 4.81E−26 |
| X11787 | rs10865398 | 1.49E−23 |
| X11787 | rs11126417 | 1.16E−22 |
| X11787 | rs11688718 | 9.37E−23 |
| X11787 | rs11884776 | 5.89E−35 |
| X11787 | rs11894953 | 5.26E−19 |
| X11787 | rs12052539 | 7.17E−24 |
| X11787 | rs12478346 | 2.36E−18 |
| X11787 | rs12624267 | 6.27E−23 |
| X11787 | rs12713798 | 3.17E−21 |
| X11787 | rs13017182 | 1.61E−26 |
| X11787 | rs13384952 | 1.11E−33 |
| X11787 | rs13386124 | 1.06E−22 |
| X11787 | rs13391552 | 6.27E−36 |
| X11787 | rs1403284 | 2.15E−35 |
| X11787 | rs17008991 | 2.42E−12 |
| X11787 | rs17009372 | 1.19E−16 |
| X11787 | rs17110192 | 1.08E−21 |
| X11787 | rs17110321 | 7.30E−23 |
| X11787 | rs17349049 | 1.24E−14 |
| X11787 | rs17350188 | 5.20E−19 |
| X11787 | rs17434655 | 6.24E−17 |
| X11787 | rs1806683 | 7.03E−23 |
| X11787 | rs1918863 | 5.86E−32 |
| X11787 | rs2070581 | 1.52E−08 |
| X11787 | rs2421574 | 2.39E−25 |
| X11787 | rs2567603 | 3.10E−20 |
| X11787 | rs3813227 | 8.61E−34 |
| X11787 | rs3813230 | 1.01E−10 |
| X11787 | rs4086116 | 2.15E−22 |
| X11787 | rs4346412 | 1.06E−23 |
| X11787 | rs4852316 | 3.71E−24 |
| X11787 | rs4852939 | 4.06E−24 |
| X11787 | rs6546826 | 1.81E−20 |
| X11787 | rs6706409 | 2.24E−21 |
| X11787 | rs6720094 | 2.43E−20 |
| X11787 | rs6745480 | 3.60E−32 |
| X11787 | rs6746971 | 7.00E−21 |
| X11787 | rs6747145 | 6.05E−22 |
| X11787 | rs6755500 | 5.74E−20 |
| X11787 | rs6759452 | 3.55E−27 |
| X11787 | rs7560272 | 1.56E−21 |
| X11787 | rs7566315 | 2.61E−25 |
| X11787 | rs7574291 | 2.05E−18 |
| X11787 | rs7576824 | 2.15E−22 |
| X11787 | rs7585004 | 8.65E−32 |
| X11787 | rs7594485 | 3.44E−11 |
| X11787 | rs7598660 | 1.58E−24 |
| X11787 | rs7606947 | 9.58E−25 |
| X11787 | rs7607014 | 7.51E−34 |
| X11787 | rs7896133 | 3.97E−26 |
| X11787 | rs9332093 | 1.11E−17 |
| X11787 | rs9332245 | 7.09E−21 |
| X11792 | rs4253252 | 1.60E−10 |
| X11792 | rs2937754 | 4.69E−07 |
| X11793 | rs6742078 | 1.03E−22 |
| X11793 | rs887829 | 2.59E−26 |
| X11793 | rs10179091 | 2.39E−13 |
| X11793 | rs10197460 | 5.52E−11 |
| X11793 | rs11695484 | 1.60E−20 |
| X11793 | rs11891311 | 4.54E−16 |
| X11793 | rs2602379 | 2.53E−09 |
| X11793 | rs2602380 | 8.00E−09 |
| X11793 | rs2741021 | 3.90E−14 |
| X11793 | rs2741045 | 3.09E−14 |
| X11793 | rs3755319 | 2.23E−19 |
| X11793 | rs3806596 | 1.80E−20 |
| X11793 | rs3806597 | 1.24E−20 |
| X11793 | rs4294999 | 5.10E−20 |
| X11793 | rs4663965 | 2.87E−19 |
| X11793 | rs6714634 | 1.68E−19 |
| X11793 | rs6715325 | 9.73E−15 |
| X11793 | rs6736508 | 7.72E−15 |
| X11793 | rs6744284 | 3.48E−16 |
| X11793 | rs6753320 | 1.19E−13 |
| X11793 | rs6754100 | 4.67E−10 |
| X11793 | rs6759892 | 2.11E−12 |
| X11793 | rs6761246 | 1.76E−09 |
| X11793 | rs7563561 | 1.43E−14 |
| X11793 | rs7564935 | 2.82E−15 |
| X11793 | rs7587916 | 2.25E−09 |
| X11793 | rs7608175 | 9.54E−15 |
| X11795 | rs9506615 | 1.388E−06 |
| X11799 | rs358231 | 2.87E−17 |
| X11799 | rs10021978 | 8.96E−07 |
| X11799 | rs358253 | 1.31E−15 |
| X11799 | rs358260 | 1.20E−16 |
| X11799 | rs430976 | 3.75E−08 |
| X11805 | rs10475541 | 1.573E−06 |
| X11809 | rs17008568 | 8.73E−07 |
| X11818 | rs196676 | 1.31E−07 |
| X11820 | rs2298423 | 3.18E−07 |
| X11826 | rs7111693 | 4.508E−06 |
| X11843 | rs690526 | 8.88E−08 |
| X11845 | rs10895514 | 4.085E−06 |
| X11847 | rs2432626 | 1.433E−06 |
| X11849 | rs7227515 | 3.843E−06 |
| X11850 | rs2003334 | 3.816E−06 |
| X11852 | rs895900 | 1.696E−06 |
| X11858 | rs1849474 | 9.87E−08 |
| X11859 | rs196703 | 5.813E−06 |
| X11876 | rs13190556 | 1.773E−06 |
| X11880 | rs4149056 | 6.73E−07 |
| X12013 | rs10493639 | 4.277E−06 |
| X12029 | rs7555956 | 3.307E−06 |
| X12038 | rs913112 | 9.827E−06 |
| X12039 | rs4908527 | 1.03E−07 |
| X12056 | rs1345015 | 3.069E−06 |
| X12063 | rs4149056 | 5.22E−20 |
| X12063 | rs10242455 | 1.47E−45 |
| X12063 | rs4149081 | 1.43E−18 |
| X12063 | rs10953286 | 1.71E−16 |
| X12063 | rs11045818 | 1.25E−07 |
| X12063 | rs11045819 | 5.15E−07 |
| X12063 | rs11045821 | 3.14E−09 |
| X12063 | rs11045825 | 1.65E−09 |
| X12063 | rs11045872 | 2.51E−09 |
| X12063 | rs11045879 | 1.76E−18 |
| X12063 | rs11045907 | 2.03E−08 |
| X12063 | rs11045908 | 2.27E−09 |
| X12063 | rs11045913 | 4.90E−09 |
| X12063 | rs11045953 | 4.02E−09 |
| X12063 | rs11734 | 9.52E−21 |
| X12063 | rs11769698 | 1.65E−11 |
| X12063 | rs12705036 | 2.48E−07 |
| X12063 | rs12812279 | 5.25E−09 |
| X12063 | rs13239596 | 2.36E−07 |
| X12063 | rs13310534 | 7.56E−08 |
| X12063 | rs1357319 | 4.72E−26 |
| X12063 | rs16923647 | 1.97E−11 |
| X12063 | rs17161652 | 1.53E−08 |
| X12063 | rs17161662 | 3.29E−08 |
| X12063 | rs17161692 | 5.64E−32 |
| X12063 | rs17161698 | 1.12E−07 |
| X12063 | rs17161726 | 1.43E−22 |
| X12063 | rs1851426 | 5.10E−21 |
| X12063 | rs2003499 | 1.65E−10 |
| X12063 | rs2014764 | 2.52E−17 |
| X12063 | rs2072181 | 6.98E−17 |
| X12063 | rs2169969 | 2.47E−09 |
| X12063 | rs2222411 | 3.87E−28 |
| X12063 | rs2240384 | 2.46E−19 |
| X12063 | rs2293256 | 4.47E−21 |
| X12063 | rs2687079 | 2.05E−24 |
| X12063 | rs2687145 | 1.58E−18 |
| X12063 | rs2740565 | 2.76E−24 |
| X12063 | rs2740566 | 1.63E−17 |
| X12063 | rs2741872 | 8.43E−19 |
| X12063 | rs2900476 | 2.75E−10 |
| X12063 | rs3735453 | 2.05E−38 |

TABLE 2-continued

| UNKNOWN | ASSOCIATING SNP | PVAL_SNP |
|---|---|---|
| X12063 | rs3764815 | 4.90E−10 |
| X12063 | rs3794319 | 1.25E−08 |
| X12063 | rs3800960 | 3.65E−08 |
| X12063 | rs41385645 | 3.29E−18 |
| X12063 | rs4149057 | 5.60E−09 |
| X12063 | rs4149058 | 5.18E−11 |
| X12063 | rs4236542 | 4.64E−10 |
| X12063 | rs4646453 | 1.61E−08 |
| X12063 | rs472660 | 1.48E−11 |
| X12063 | rs4729568 | 9.66E−08 |
| X12063 | rs4836309 | 6.32E−07 |
| X12063 | rs4836313 | 7.58E−07 |
| X12063 | rs501275 | 1.23E−10 |
| X12063 | rs642761 | 9.09E−09 |
| X12063 | rs6651108 | 3.12E−18 |
| X12063 | rs678040 | 1.85E−11 |
| X12063 | rs6945984 | 7.59E−23 |
| X12063 | rs6955490 | 5.99E−11 |
| X12063 | rs6957987 | 2.55E−13 |
| X12063 | rs6960432 | 8.59E−08 |
| X12063 | rs776746 | 6.86E−36 |
| X12063 | rs7778571 | 4.26E−08 |
| X12063 | rs7787830 | 2.31E−07 |
| X12063 | rs7793425 | 1.26E−07 |
| X12063 | rs7962263 | 6.97E−07 |
| X12063 | rs7967303 | 1.31E−08 |
| X12063 | rs952319 | 1.95E−14 |
| X12063 | rs9969217 | 8.25E−09 |
| X12092 | rs4488133 | 2.24E−281 |
| X12092 | rs1061135 | 1.07E−14 |
| X12092 | rs1061437 | 3.78E−133 |
| X12092 | rs10736129 | 2.87E−152 |
| X12092 | rs10883094 | 1.72E−96 |
| X12092 | rs11189513 | 1.43E−07 |
| X12092 | rs11189552 | 4.29E−29 |
| X12092 | rs11189559 | 2.78E−16 |
| X12092 | rs11189569 | 2.82E−16 |
| X12092 | rs11189577 | 3.61E−17 |
| X12092 | rs11189600 | 3.06E−158 |
| X12092 | rs11189602 | 3.39E−13 |
| X12092 | rs11189615 | 1.21E−07 |
| X12092 | rs11189628 | 8.24E−08 |
| X12092 | rs11599208 | 3.97E−09 |
| X12092 | rs11814584 | 3.43E−27 |
| X12092 | rs12763326 | 3.37E−118 |
| X12092 | rs17109634 | 3.74E−29 |
| X12092 | rs1739 | 8.89E−202 |
| X12092 | rs2095365 | 5.82E−07 |
| X12092 | rs2147897 | 3.86E−264 |
| X12092 | rs2147901 | 1.30E−117 |
| X12092 | rs2274248 | 3.53E−152 |
| X12092 | rs2296435 | 1.75E−121 |
| X12092 | rs2862297 | 1.26E−27 |
| X12092 | rs3830020 | 1.09E−205 |
| X12092 | rs4345897 | 1.20E−207 |
| X12092 | rs4400721 | 1.28E−139 |
| X12092 | rs4491153 | 5.90E−14 |
| X12092 | rs4551689 | 7.21E−188 |
| X12092 | rs4568939 | 1.65E−57 |
| X12092 | rs4611142 | 2.38E−08 |
| X12092 | rs4917817 | 2.99E−07 |
| X12092 | rs4917818 | 1.99E−12 |
| X12092 | rs4919209 | 2.65E−13 |
| X12092 | rs6584185 | 3.37E−13 |
| X12092 | rs6584206 | 7.82E−10 |
| X12092 | rs7072216 | 3.88E−275 |
| X12092 | rs7075856 | 8.63E−07 |
| X12092 | rs747022 | 4.86E−08 |
| X12092 | rs765456 | 1.45E−12 |
| X12092 | rs7894393 | 3.40E−15 |
| X12092 | rs7896828 | 6.99E−185 |
| X12092 | rs7907555 | 2.18E−229 |
| X12092 | rs7909297 | 3.64E−14 |
| X12092 | rs7914401 | 1.70E−123 |
| X12092 | rs7924303 | 1.34E−216 |
| X12093 | rs6710438 | 4.24E−18 |
| X12093 | rs4488133 | 1.35E−27 |
| X12093 | rs7598396 | 1.73E−19 |
| X12093 | rs6753344 | 1.39E−20 |
| X12093 | rs10190002 | 6.79E−11 |
| X12093 | rs10496190 | 1.61E−09 |
| X12093 | rs1052161 | 5.57E−10 |
| X12093 | rs1052162 | 5.40E−20 |
| X12093 | rs1061437 | 2.13E−18 |
| X12093 | rs10736129 | 5.47E−21 |
| X12093 | rs1083922 | 5.63E−12 |
| X12093 | rs10865398 | 2.71E−11 |
| X12093 | rs10883094 | 9.80E−15 |
| X12093 | rs11126417 | 1.68E−09 |
| X12093 | rs11189552 | 2.46E−07 |
| X12093 | rs11189600 | 5.78E−17 |
| X12093 | rs11688718 | 5.23E−11 |
| X12093 | rs11884776 | 6.14E−21 |
| X12093 | rs11894953 | 3.24E−08 |
| X12093 | rs12052539 | 1.58E−10 |
| X12093 | rs12478346 | 1.53E−11 |
| X12093 | rs12624267 | 9.37E−11 |
| X12093 | rs12631271 | 4.71E−07 |
| X12093 | rs12713798 | 8.29E−10 |
| X12093 | rs12763326 | 4.13E−16 |
| X12093 | rs13017182 | 1.32E−13 |
| X12093 | rs13384952 | 3.22E−18 |
| X12093 | rs13386124 | 7.74E−12 |
| X12093 | rs13391552 | 8.86E−22 |
| X12093 | rs1403284 | 2.44E−19 |
| X12093 | rs17008991 | 2.87E−07 |
| X12093 | rs17009372 | 7.86E−07 |
| X12093 | rs17022443 | 4.62E−08 |
| X12093 | rs17288261 | 4.89E−07 |
| X12093 | rs17349049 | 1.96E−08 |
| X12093 | rs17350188 | 2.21E−08 |
| X12093 | rs1739 | 1.53E−21 |
| X12093 | rs17434655 | 2.54E−08 |
| X12093 | rs17668735 | 4.04E−07 |
| X12093 | rs1806683 | 7.13E−10 |
| X12093 | rs1918863 | 6.59E−20 |
| X12093 | rs2147897 | 1.24E−26 |
| X12093 | rs2147901 | 4.00E−16 |
| X12093 | rs2274248 | 2.67E−22 |
| X12093 | rs2296435 | 1.29E−16 |
| X12093 | rs2421574 | 8.36E−12 |
| X12093 | rs2567603 | 2.87E−09 |
| X12093 | rs3813227 | 6.80E−18 |
| X12093 | rs3830020 | 2.10E−21 |
| X12093 | rs4345897 | 3.07E−20 |
| X12093 | rs4346412 | 6.52E−21 |
| X12093 | rs4400721 | 1.31E−17 |
| X12093 | rs4551689 | 9.79E−19 |
| X12093 | rs4568939 | 4.96E−10 |
| X12093 | rs4852316 | 5.44E−11 |
| X12093 | rs4852939 | 3.73E−11 |
| X12093 | rs6546826 | 8.00E−14 |
| X12093 | rs6706409 | 1.13E−13 |
| X12093 | rs6720094 | 7.43E−12 |
| X12093 | rs6745480 | 3.26E−17 |
| X12093 | rs6746971 | 3.15E−10 |
| X12093 | rs6747145 | 6.50E−11 |
| X12093 | rs6755500 | 9.22E−09 |
| X12093 | rs6759452 | 3.49E−13 |
| X12093 | rs6781351 | 2.08E−07 |
| X12093 | rs6782309 | 3.68E−07 |
| X12093 | rs7072216 | 5.69E−26 |
| X12093 | rs7560272 | 7.35E−12 |
| X12093 | rs7566315 | 2.47E−13 |
| X12093 | rs7574291 | 2.31E−11 |
| X12093 | rs7576824 | 4.68E−10 |
| X12093 | rs7585004 | 6.65E−17 |
| X12093 | rs7598660 | 8.72E−11 |
| X12093 | rs7606947 | 5.15E−12 |
| X12093 | rs7607014 | 2.58E−19 |
| X12093 | rs7896828 | 6.03E−19 |
| X12093 | rs7907555 | 2.72E−24 |
| X12093 | rs7914401 | 3.07E−17 |
| X12093 | rs7924303 | 2.44E−23 |
| X12094 | rs2596210 | 3.32E−07 |
| X12095 | rs10928512 | 2.002E−06 |

TABLE 2-continued

| UNKNOWN | ASSOCIATING SNP | PVAL_SNP |
|---|---|---|
| X12100 | rs6151896 | 3.68E−07 |
| X12116 | rs704381 | 6.66E−07 |
| X12188 | rs10026884 | 5.586E−06 |
| X12206 | rs13416390 | 6.322E−06 |
| X12212 | rs4915559 | 7.43E−07 |
| X12216 | rs2736003 | 2.59E−06 |
| X12217 | rs1383950 | 4.48E−06 |
| X12230 | rs12504564 | 1.37E−07 |
| X12231 | rs2741110 | 5.064E−06 |
| X12236 | rs6083461 | 9.04E−07 |
| X12244 | rs10508017 | 2.88E−09 |
| X12253 | rs7936703 | 3.804E−06 |
| X12261 | rs2576810 | 6.29E−07 |
| X12405 | rs7564502 | 3.03E−07 |
| X12407 | rs1475525 | 8.07E−07 |
| X12428 | rs3205166 | 3.394E−06 |
| X12441 | rs138832 | 1.021E−06 |
| X12442 | rs2279502 | 8.86E−08 |
| X12443 | rs13256631 | 3.53E−07 |
| X12450 | rs11760020 | 5.31E−08 |
| X12456 | rs4149056 | 8.41E−17 |
| X12456 | rs4149081 | 3.77E−15 |
| X12456 | rs11045818 | 5.11E−08 |
| X12456 | rs11045819 | 1.41E−07 |
| X12456 | rs11045821 | 5.21E−07 |
| X12456 | rs11045825 | 9.32E−07 |
| X12456 | rs11045872 | 4.80E−07 |
| X12456 | rs11045879 | 2.13E−15 |
| X12456 | rs16837493 | 7.76E−07 |
| X12456 | rs16923647 | 1.98E−07 |
| X12456 | rs2169969 | 1.74E−07 |
| X12456 | rs2900476 | 6.42E−11 |
| X12456 | rs4149057 | 7.50E−08 |
| X12456 | rs4149058 | 2.93E−10 |
| X12465 | rs7723967 | 2.239E−06 |
| X12510 | rs6710438 | 2.06E−47 |
| X12510 | rs7598396 | 1.53E−56 |
| X12510 | rs6753344 | 1.78E−52 |
| X12510 | rs10190002 | 9.18E−27 |
| X12510 | rs10193032 | 5.74E−17 |
| X12510 | rs10496190 | 6.98E−25 |
| X12510 | rs1052161 | 1.15E−27 |
| X12510 | rs1052162 | 1.30E−54 |
| X12510 | rs1083922 | 1.56E−34 |
| X12510 | rs10865398 | 7.80E−31 |
| X12510 | rs11126417 | 2.72E−31 |
| X12510 | rs11688718 | 3.57E−27 |
| X12510 | rs11884776 | 3.15E−53 |
| X12510 | rs11894953 | 1.12E−25 |
| X12510 | rs12052539 | 7.17E−33 |
| X12510 | rs12467259 | 7.83E−07 |
| X12510 | rs12478346 | 4.31E−27 |
| X12510 | rs12624267 | 6.31E−31 |
| X12510 | rs12713798 | 3.38E−30 |
| X12510 | rs13017182 | 1.08E−37 |
| X12510 | rs13384952 | 6.74E−55 |
| X12510 | rs13386124 | 1.17E−31 |
| X12510 | rs13391552 | 1.47E−54 |
| X12510 | rs1403284 | 9.86E−55 |
| X12510 | rs17008991 | 8.76E−16 |
| X12510 | rs17009372 | 1.46E−21 |
| X12510 | rs17349049 | 2.55E−18 |
| X12510 | rs17350188 | 3.16E−27 |
| X12510 | rs17434655 | 2.92E−25 |
| X12510 | rs1806683 | 8.27E−30 |
| X12510 | rs1881244 | 2.31E−11 |
| X12510 | rs1918863 | 4.36E−52 |
| X12510 | rs2070581 | 5.16E−13 |
| X12510 | rs2421574 | 4.43E−34 |
| X12510 | rs2567603 | 2.21E−31 |
| X12510 | rs3813227 | 1.19E−50 |
| X12510 | rs3813230 | 1.36E−17 |
| X12510 | rs4346412 | 7.48E−32 |
| X12510 | rs4514898 | 2.68E−10 |
| X12510 | rs4852316 | 2.12E−33 |
| X12510 | rs4852939 | 7.79E−31 |
| X12510 | rs6546826 | 4.77E−31 |
| X12510 | rs6706409 | 2.47E−33 |
| X12510 | rs6720094 | 9.51E−31 |
| X12510 | rs6745480 | 3.83E−49 |
| X12510 | rs6746971 | 2.28E−25 |
| X12510 | rs6747145 | 1.91E−31 |
| X12510 | rs6755500 | 4.32E−28 |
| X12510 | rs6759452 | 2.67E−38 |
| X12510 | rs7560272 | 1.15E−30 |
| X12510 | rs7566315 | 6.61E−34 |
| X12510 | rs7570391 | 7.24E−09 |
| X12510 | rs7574291 | 4.52E−28 |
| X12510 | rs7576824 | 7.94E−29 |
| X12510 | rs7585004 | 4.20E−48 |
| X12510 | rs7594485 | 1.33E−16 |
| X12510 | rs7598660 | 7.32E−30 |
| X12510 | rs7606947 | 1.05E−33 |
| X12510 | rs7607014 | 7.94E−56 |
| X12524 | rs10497004 | 1.663E−06 |
| X12544 | rs798598 | 6.054E−06 |
| X12556 | rs1550642 | 6.63E−07 |
| X12627 | rs3798720 | 1.86E−07 |
| X12644 | rs6505683 | 4.49E−07 |
| X12645 | rs168190 | 4.09E−07 |
| X12680 | rs7477871 | 3.138E−06 |
| X12696 | rs1936074 | 6.65E−07 |
| X12704 | rs13129177 | 7.26E−07 |
| X12711 | rs11242244 | 3.60E−07 |
| X12717 | rs6695534 | 1.637E−06 |
| X12719 | rs11670870 | 1.147E−06 |
| X12726 | rs1015150 | 5.659E−06 |
| X12728 | rs11831314 | 2.252E−06 |
| X12729 | rs13246970 | 8.53E−08 |
| X12734 | rs12725733 | 1.48E−06 |
| X12740 | rs2301920 | 1.904E−06 |
| X12749 | rs6507247 | 5.04E−07 |
| X12771 | rs802441 | 6.40E−07 |
| X12776 | rs6429539 | 3.889E−06 |
| X12786 | rs17406291 | 7.00E−07 |
| X12798 | rs316020 | 1.73E−72 |
| X12798 | rs2448295 | 4.77E−34 |
| X12798 | rs2448298 | 2.36E−51 |
| X12798 | rs2619268 | 2.48E−14 |
| X12798 | rs315988 | 7.33E−41 |
| X12798 | rs316000 | 1.16E−25 |
| X12798 | rs316007 | 6.99E−38 |
| X12798 | rs316013 | 6.89E−38 |
| X12798 | rs316015 | 3.93E−35 |
| X12798 | rs316025 | 4.31E−22 |
| X12798 | rs316034 | 2.31E−27 |
| X12798 | rs316035 | 5.83E−33 |
| X12798 | rs316167 | 7.68E−09 |
| X12798 | rs316169 | 5.76E−09 |
| X12798 | rs316170 | 5.35E−09 |
| X12798 | rs384156 | 3.94E−08 |
| X12798 | rs393271 | 1.10E−08 |
| X12798 | rs409952 | 6.67E−07 |
| X12798 | rs410569 | 1.10E−08 |
| X12798 | rs415897 | 1.09E−08 |
| X12798 | rs435421 | 4.8E−07 |
| X12798 | rs446809 | 8.24E−09 |
| X12798 | rs505111 | 2.85E−09 |
| X12798 | rs515140 | 3.58E−36 |
| X12798 | rs533452 | 1.85E−11 |
| X12798 | rs596881 | 1.42E−57 |
| X12798 | rs667538 | 5.01E−09 |
| X12816 | rs13275783 | 1.704E−06 |
| X12830 | rs12517012 | 2.23E−07 |
| X12844 | rs465226 | 1.153E−06 |
| X12847 | rs9517904 | 4.538E−06 |
| X12850 | rs11019976 | 3.68E−08 |
| X12851 | rs11029926 | 4.43E−07 |
| X12855 | rs3820881 | 6.136E−06 |
| X12990 | rs2524299 | 9.74E−08 |
| X13069 | rs1958375 | 1.257E−06 |
| X13183 | rs10935295 | 3.21E−07 |
| X13215 | rs11880261 | 4.20E−08 |
| X13372 | rs1995973 | 1.996E−06 |
| X13429 | rs4149056 | 4.86E−22 |
| X13429 | rs4149081 | 6.57E−20 |

TABLE 2-continued

| UNKNOWN | ASSOCIATING SNP | PVAL_SNP |
|---|---|---|
| X13429 | rs10841753 | 4.44E−09 |
| X13429 | rs11045512 | 1.13E−07 |
| X13429 | rs11045521 | 2.91E−07 |
| X13429 | rs11045773 | 3.51E−07 |
| X13429 | rs11045818 | 1.97E−09 |
| X13429 | rs11045819 | 5.94E−10 |
| X13429 | rs11045821 | 8.96E−11 |
| X13429 | rs11045825 | 3.79E−10 |
| X13429 | rs11045872 | 8.18E−10 |
| X13429 | rs11045879 | 1.04E−19 |
| X13429 | rs11045907 | 1.13E−09 |
| X13429 | rs11045908 | 4.64E−09 |
| X13429 | rs11045913 | 8.89E−12 |
| X13429 | rs12812279 | 1.11E−11 |
| X13429 | rs16923647 | 1.46E−11 |
| X13429 | rs2169969 | 6.42E−11 |
| X13429 | rs2900476 | 1.82E−16 |
| X13429 | rs4149057 | 5.36E−08 |
| X13429 | rs4149058 | 5.13E−15 |
| X13431 | rs2286963 | 2.68E−33 |
| X13431 | rs10932321 | 1.92E−15 |
| X13431 | rs11889646 | 2.09E−18 |
| X13431 | rs1396828 | 7.98E−16 |
| X13431 | rs1472955 | 8.82E−12 |
| X13431 | rs1509569 | 1.40E−24 |
| X13431 | rs2041688 | 8.58E−19 |
| X13431 | rs2539862 | 3.88E−14 |
| X13431 | rs2723222 | 7.77E−21 |
| X13431 | rs2723225 | 3.03E−22 |
| X13431 | rs3764913 | 6.93E−28 |
| X13431 | rs6725084 | 1.84E−16 |
| X13431 | rs6735154 | 9.39E−19 |
| X13431 | rs7557847 | 1.49E−27 |
| X13431 | rs7570090 | 2.16E−24 |
| X13431 | rs7583039 | 6.99E−19 |
| X13431 | rs7593548 | 2.29E−19 |
| X13431 | rs7596691 | 4.41E−12 |
| X13435 | rs2745454 | 8.22E−07 |
| X13477 | rs6753344 | 1.04E−07 |
| X13496 | rs1867237 | 1.255E−06 |
| X13548 | rs6882355 | 3.548E−06 |
| X13549 | rs17122693 | 2.68E−06 |
| X13553 | rs17135372 | 4.136E−06 |
| X13619 | rs1478903 | 6.588E−06 |
| X13640 | rs7716072 | 2.288E−06 |
| X13671 | rs4684510 | 6.78E−07 |
| X13741 | rs3014887 | 1.66E−06 |
| X13859 | rs17817518 | 4.137E−06 |
| X14056 | rs2224768 | 1.642E−06 |
| X14057 | rs6659821 | 3.606E−06 |
| X14086 | rs4351 | 4.02E−09 |
| X14189 | rs4351 | 2.39E−16 |
| X14189 | rs4343 | 1.48E−16 |
| X14189 | rs4325 | 2.27E−16 |
| X14189 | rs1029765 | 9.57E−07 |
| X14189 | rs12494751 | 6.98E−07 |
| X14189 | rs4293 | 4.56E−10 |
| X14189 | rs4324 | 2.70E−15 |
| X14189 | rs4329 | 8.58E−15 |
| X14189 | rs4968762 | 1.93E−07 |
| X14189 | rs558240 | 2.55E−07 |
| X14189 | rs6415419 | 2.44E−07 |
| X14189 | rs6468424 | 1.09E−07 |
| X14189 | rs651007 | 9.76E−08 |
| X14205 | rs4351 | 3.97E−14 |
| X14205 | rs4343 | 2.28E−13 |
| X14205 | rs4325 | 6.40E−13 |
| X14205 | rs4324 | 2.81E−11 |
| X14205 | rs4329 | 1.77E−10 |
| X14205 | rs4736744 | 8.70E−07 |
| X14208 | rs4351 | 4.58E−15 |
| X14208 | rs4343 | 1.92E−13 |
| X14208 | rs4325 | 2.61E−13 |
| X14208 | rs11190338 | 9.54E−07 |
| X14208 | rs17061987 | 3.11E−07 |
| X14208 | rs4293 | 1.92E−09 |
| X14208 | rs4324 | 7.82E−13 |
| X14208 | rs4329 | 7.23E−12 |
| X14208 | rs4895946 | 5.15E−07 |
| X14208 | rs4897621 | 9.22E−07 |
| X14208 | rs9375929 | 3.49E−07 |
| X14304 | rs4351 | 3.87E−12 |
| X14304 | rs4343 | 6.60E−12 |
| X14304 | rs4325 | 2.68E−12 |
| X14304 | rs4293 | 9.95E−08 |
| X14304 | rs4324 | 8.40E−12 |
| X14304 | rs4329 | 7.85E−11 |
| X14304 | rs8066722 | 7.87E−07 |
| X14374 | rs1374273 | 4.19E−07 |
| X14450 | rs644045 | 1.015E−05 |
| X14473 | rs7828363 | 1.86E−07 |
| X14478 | rs7239408 | 4.673E−06 |
| X14486 | rs10079220 | 1.79E−07 |
| X14541 | rs1026975 | 9.57E−07 |
| X14588 | rs6853408 | 7.24E−07 |
| X14625 | rs6558292 | 4.18E−09 |
| X14626 | rs4149056 | 2.91E−13 |
| X14626 | rs4149081 | 2.08E−13 |
| X14626 | rs10841753 | 1.02E−07 |
| X14626 | rs11045767 | 4.9E−07 |
| X14626 | rs11045787 | 5.70E−08 |
| X14626 | rs11045818 | 7.49E−10 |
| X14626 | rs11045819 | 5.60E−10 |
| X14626 | rs11045821 | 1.55E−09 |
| X14626 | rs11045825 | 2.76E−08 |
| X14626 | rs11045872 | 9.22E−10 |
| X14626 | rs11045879 | 4.19E−13 |
| X14626 | rs11045907 | 1.44E−09 |
| X14626 | rs11045908 | 1.23E−07 |
| X14626 | rs11045913 | 8.46E−11 |
| X14626 | rs12812279 | 8.14E−09 |
| X14626 | rs16923647 | 1.42E−08 |
| X14626 | rs2169969 | 3.39E−09 |
| X14626 | rs2900476 | 6.26E−11 |
| X14626 | rs4149058 | 4.05E−09 |
| X14632 | rs10484128 | 7.48E−07 |
| X14658 | rs11265831 | 1.221E−06 |
| X14662 | rs12093439 | 1.83E−07 |
| X14663 | rs7914737 | 2.42E−07 |
| X14745 | rs6560714 | 5.15E−07 |
| X14977 | rs16834673 | 1.163E−06 |

TABLE 3

| UN-KNOWN | SIGNIF GGM CORR PARTNER | PVAL GGM | BEST ASSO-CIATING SNP | LOCUS dbSNP | DESC LOCUS | PVAL SNP |
|---|---|---|---|---|---|---|
| X01911 | piperine | 3.28E−118 | rs4680 | COMT | catechol-O-methyltransferase | 5.80E−011 |
|  | X11847 | 2.41E−047 |  |  |  |  |
|  | X11849 | 1.09E−038 |  |  |  |  |
|  | X11593 | 2.98E−038 |  |  |  |  |
|  | X11485 | 8.36E−010 |  |  |  |  |
|  | X12206 | 4.77E−007 |  |  |  |  |

TABLE 3-continued

| UN-KNOWN | SIGNIF GGM CORR PARTNER | PVAL GGM | BEST ASSOCIATING SNP | LOCUS dbSNP | DESC LOCUS | PVAL SNP |
|---|---|---|---|---|---|---|
| X02249 | @carboxy4methyl5propyl-2furanpropanoateCMPF | 5.23E−032 | rs867212 | GRAMD4 | | 1.50E−006 |
| | eicosapentaenoateEPA205n3 | 9.64E−021 | | | | |
| | theobromine | 7.53E−009 | | | | |
| | X02269 | 3.11E−008 | | | | |
| X02269 | X11469 | 0 | rs6583967 | CYP2C8 | | 4.84E−007 |
| | @3carboxy4methyl5propyl-2furanpropanoateCMPF | 2.04E−045 | | | | |
| | X02249 | 3.11E−008 | | | | |
| X02973 | erythrose | 1.24E−017 | rs12652460 | | | 2.16E−006 |
| | ascorbateVitaminC | 5.26E−011 | | | | |
| | threonate | 5.24E−010 | | | | |
| | X13619 | 2.09E−008 | | | | |
| | X04357 | 3.85E−007 | | | | |
| X03003 | X10810 | 1.66E−010 | rs10879287 | | | 6.13E−007 |
| | erythrose | 1.19E−009 | | | | |
| X03056 | X11422 | 1.55E−008 | rs4240520 | PAOX | | 3.03E−008 |
| | isobutyrylcarnitine | 1.41E−007 | | | | |
| | citrulline | 7.89E−007 | | | | |
| X03088 | arginine | 6.36E−018 | rs7329126 | | | 1.32E−006 |
| | citrulline | 2.02E−009 | | | | |
| | phosphate | 2.00E−007 | | | | |
| X03090 | | | rs4952293 | | | 9.08E−007 |
| X03094 | @2palmitoylglycerophosphocholine | 4.97E−013 | rs3741298 | | | 1.49E−009 |
| | cholesterol | 1.49E−010 | | | | |
| | citrate | 1.39E−008 | | | | |
| | @1stearoylglycerophosphoinositol | 1.81E−007 | | | | |
| X04357 | X12786 | 9.02E−096 | rs1953661 | | | 3.80E−006 |
| | erythrose | 4.93E−019 | | | | |
| | fructose | 5.26E−014 | | | | |
| | threonate | 3.04E−010 | | | | |
| | threonine | 8.87E−008 | | | | |
| | aspartate | 1.10E−007 | | | | |
| | X02973 | 3.85E−007 | | | | |
| | @1palmitoylglycerophosphoinositol | 6.32E−007 | | | | |
| X04494 | | | rs9365108 | | | 4.65E−006 |
| X04495 | @2aminobutyrate | 2.85E−041 | rs7634246 | | | 1.25E−006 |
| | creatine | 1.45E−026 | | | | |
| | @2hydroxybutyrateAHB | 2.84E−012 | | | | |
| | X12244 | 5.33E−012 | | | | |
| | X12556 | 4.26E−008 | | | | |
| | X13435 | 5.76E−008 | | | | |
| X04498 | X05426 | 5.71E−016 | rs3848141 | UNC13C | | 2.59E−007 |
| | @2hydroxyisobutyrate | 7.67E−009 | | | | |
| | threitol | 6.39E−008 | | | | |
| | urea | 1.99E−007 | | | | |
| X04499 | X05491 | 2.48E−019 | rs17076477 | | | 1.15E−007 |
| X04500 | | | rs2920861 | | | 1.08E−006 |
| X04515 | | | rs7785988 | LOC100286906 | | 1.08E−006 |
| X05426 | X12039 | 7.82E−037 | rs1881514 | SPON1 | | 1.67E−007 |
| | X04498 | 5.71E−016 | | | | |
| | quinate | 2.10E−007 | | | | |
| X05491 | X04499 | 2.48E−019 | rs16823855 | | | 6.43E−007 |
| | X13372 | 2.81E−008 | | | | |
| | erythrose | 1.34E−007 | | | | |
| X05907 | X10395 | 7.52E−048 | rs1635181 | THSD7A | | 3.76E−006 |
| | X06226 | 2.86E−008 | | | | |
| X06126 | pcresolsulfate | 6.57E−074 | rs353807 | | | 8.06E−007 |
| | threitol | 4.94E−007 | | | | |
| X06226 | X10395 | 1.17E−013 | rs12413935 | NRG3 | neuregulin 3 | 4.09E−011 |
| | X09026 | 2.58E−012 | | | | |
| | X05907 | 2.86E−008 | | | | |
| X06227 | acetylphosphate | 4.28E−084 | rs1695945 | | | 6.75E−007 |
| X06246 | alanine | 2.20E−065 | rs2219008 | | | 5.56E−007 |
| | X14977 | 1.46E−008 | | | | |
| X06267 | citrulline | 1.25E−021 | rs17138748 | LHFPL3 | | 4.23E−006 |
| | X10810 | 1.26E−007 | | | | |
| X06307 | X11805 | 4.70E−042 | rs9316180 | CPB2 | | 4.93E−009 |
| | X14205 | 2.24E−016 | | | | |
| | DSGEGDFXAEGGGVR | 1.36E−007 | | | | |
| | X12798 | 2.74E−007 | | | | |
| X06350 | | | rs12028243 | | | 6.31E−007 |
| X06351 | | | rs13097461 | | | 9.91E−007 |
| X07765 | | | rs4687417 | ATP13A5 | | 9.67E−007 |
| X08402 | X10510 | 7.78E−067 | rs4902250 | SYNE2 | | 1.18E−009 |

TABLE 3-continued

| UN-KNOWN | SIGNIF GGM CORR PARTNER | PVAL GGM | BEST ASSOCIATING SNP | LOCUS dbSNP | DESC LOCUS | PVAL SNP |
|---|---|---|---|---|---|---|
| X08766 | | | rs11621845 | CCDC88C | | 1.19E−006 |
| X08988 | glycine | 2.40E−024 | rs1398806 | | | 9.03E−007 |
| | alanine | 1.46E−010 | | | | |
| X09026 | X10395 | 2.56E−012 | rs9320134 | | | 1.32E−007 |
| | X06226 | 2.58E−012 | | | | |
| X09108 | glutamine | 5.89E−012 | rs10972022 | UBAP1 | | 1.51E−006 |
| X09706 | X13619 | 6.34E−112 | rs803422 | MTHFD1L | | 3.64E−007 |
| | urea | 4.61E−111 | | | | |
| | @2hydroxyisobutyrate | 1.61E−011 | | | | |
| X09789 | X12253 | 9.90E−025 | rs2588976 | | | 1.49E−007 |
| | X12039 | 6.63E−011 | | | | |
| | @4vinylphenolsulfate | 7.35E−011 | | | | |
| | homostachydrine | 3.17E−010 | | | | |
| X10346 | | | rs6432834 | CSRNP3 | | 1.76E−006 |
| X10395 | X05907 | 7.52E−048 | rs10497458 | | | 2.54E−008 |
| | X06226 | 1.17E−013 | | | | |
| | X09026 | 2.56E−012 | | | | |
| | ascorbateVitaminC | 7.41E−007 | | | | |
| X10419 | cholesterol | 2.70E−065 | rs10260816 | | | 2.78E−006 |
| | X10510 | 6.57E−028 | | | | |
| | X10500 | 9.58E−017 | | | | |
| | phosphate | 1.75E−009 | | | | |
| | acetylphosphate | 1.74E−007 | | | | |
| X10429 | | | rs6767775 | | | 4.03E−006 |
| X10500 | cholesterol | 1.67E−019 | rs16946189 | | | 1.76E−006 |
| | X10419 | 9.58E−017 | | | | |
| | acetylphosphate | 5.44E−008 | | | | |
| X10506 | glucose | 3.69E−014 | rs1284066 | | | 9.82E−007 |
| | lysine | 4.32E−014 | | | | |
| | aspartate | 1.22E−013 | | | | |
| | pyruvate | 2.36E−010 | | | | |
| | X13619 | 5.15E−009 | | | | |
| | serine | 2.14E−007 | | | | |
| X10510 | X08402 | 7.78E−067 | rs11856508 | | | 2.85E−007 |
| | X10419 | 6.57E−028 | | | | |
| X10675 | | | rs2279812 | | | 4.77E−007 |
| X10810 | hypoxanthine | 7.14E−014 | rs9610927 | | | 1.12E−006 |
| | X03003 | 1.66E−010 | | | | |
| | X12990 | 5.78E−008 | | | | |
| | X06267 | 1.26E−007 | | | | |
| | ascorbateVitaminC | 1.56E−007 | | | | |
| | cysteineglutathionedisulfide | 1.98E−007 | | | | |
| | X12441 | 2.26E−007 | | | | |
| X11204 | X11327 | 3.22E−270 | rs1545358 | | | 1.23E−005 |
| | bilirubinEZorZE | 2.84E−009 | | | | |
| | X11809 | 2.98E−008 | | | | |
| | octanoylcarnitine | 3.09E−007 | | | | |
| X11244 | X11443 | 8.93E−113 | rs296391 | SULT2A1; CRX | sulfotransferase family, cytosolic, 2A, dehydroepiandrosterone (DHEA)-preferring, member 1; cone-rod homeobox | 2.12E−026 |
| | X11440 | 7.62E−093 | | | | |
| | dehydroisoandrosteronesulfateDHEAS | 7.47E−037 | | | | |
| | epiandrosteronesulfate | 6.66E−016 | | | | |
| | thromboxaneB2 | 1.12E−012 | | | | |
| | X11470 | 4.12E−009 | | | | |
| X11247 | X11787 | 7.05E−007 | rs2807872 | | | 7.14E−008 |
| X11255 | @4vinylphenolsulfate | 4.99E−019 | rs8179972 | | | 1.69E−006 |
| | @2methylbutyroylcarnitine | 7.18E−019 | | | | |
| | eicosenoate201n9or11 | 1.39E−007 | | | | |
| | @4ethylphenylsulfate | 6.60E−007 | | | | |
| X11261 | linolenatealphaorgamma183n3or6 | 7.91E−081 | rs1247499 | C10orf11 | | 8.16E−007 |
| | @10undecenoate111n1 | 4.18E−008 | | | | |
| | isobutyrylcarnitine | 1.31E−007 | | | | |
| | X11880 | 3.66E−007 | | | | |
| X11299 | | | rs671938 | EYS | | 2.37E−006 |
| X11315 | | | rs7782739 | | | 1.33E−006 |
| X11317 | X11497 | 1.58E−032 | rs4575635 | KLK13 | | 8.02E−008 |
| | X12038 | 1.49E−028 | | | | |
| | X12524 | 1.52E−010 | | | | |
| X11319 | margarate170 | 1.84E−015 | rs11118895 | | | 2.90E−007 |
| | @3methoxytyrosine | 2.14E−013 | | | | |
| | @10heptadecenoate171n7 | 3.11E−009 | | | | |
| | myristoleate141n5 | 1.04E−008 | | | | |
| | @10nonadecenoate191n9 | 1.94E−007 | | | | |

TABLE 3-continued

| UN-KNOWN | SIGNIF GGM CORR PARTNER | PVAL GGM | BEST ASSOCIATING SNP | LOCUS dbSNP | DESC LOCUS | PVAL SNP |
|---|---|---|---|---|---|---|
| X11327 | X11204 | 3.22E−270 | rs7129081 | | | 7.47E−007 |
| | octanoylcarnitine | 6.97E−007 | | | | |
| X11334 | pipecolate | 5.50E−021 | rs16833988 | | | 1.73E−006 |
| | indolelactate | 1.52E−008 | | | | |
| X11374 | | | rs457075 | | | 3.39E−007 |
| X11381 | X12798 | 5.21E−010 | rs11106542 | CLLU1; CLLU1OS | | 1.36E−006 |
| | X11442 | 1.09E−007 | | | | |
| | @5oxoproline | 1.45E−007 | | | | |
| X11412 | | | rs359980 | | | 3.19E−007 |
| X11421 | X13435 | 9.93E−056 | rs12134854 | ACADM | acyl-CoA dehydrogenase, C-4 to C-12 straight chain | 1.90E−027 |
| | linoleate182n6 | 1.55E−045 | | | | |
| | octanoylcarnitine | 1.05E−040 | | | | |
| | hexanoylcarnitine | 1.00E−023 | | | | |
| X11422 | xanthine | 9.35E−110 | rs2406278 | DAB1 | | 2.70E−007 |
| | urate | 6.50E−018 | | | | |
| | hypoxanthine | 2.81E−015 | | | | |
| | X03056 | 1.55E−008 | | | | |
| X11423 | X12749 | 2.88E−150 | rs6429032 | RYR2 | | 1.43E−006 |
| X11437 | | | rs7779508 | | | 2.76E−006 |
| X11438 | @10undecenoate111n1 | 4.36E−042 | rs174456 | FADS3 | | 3.05E−006 |
| | @2hydroxyisobutyrate | 5.57E−011 | | | | |
| | @10nonadecenoate191n9 | 1.09E−009 | | | | |
| | X11847 | 1.66E−008 | | | | |
| | X11538 | 6.88E−007 | | | | |
| X11440 | X11244 | 7.62E−093 | rs296391 | SULT2A1; CRX | sulfotransferase family, cytosolic, 2A, dehydroepiandrosterone (DHEA)-preferring, member 1; cone-rod homeobox | 1.69E−043 |
| | X11445 | 1.13E−045 | | | | |
| | X11470 | 5.45E−011 | | | | |
| | epiandrosteronesulfate | 5.89E−011 | | | | |
| | X12844 | 2.73E−010 | | | | |
| X11441 | X11442 | 0 | rs6742078 | UGT1A1; UGT1A10; UGT1A3; UGT1A4; UGT1A5; UGT1A6; UGT1A7; UGT1A8; UGT1A9 | UDP glucuronosyltransferase 1 family, polypeptide A | 5.59E−030 |
| | X11530 | 1.18E−008 | | | | |
| | bilirubinZZ | 2.35E−007 | | | | |
| X11442 | X11441 | 0 | rs6742078 | UGT1A1; UGT1A10; UGT1A3; UGT1A4; UGT1A5; UGT1A6; UGT1A7; UGT1A8; UGT1A9 | UDP glucuronosyltransferase 1 family, polypeptide A | 1.19E−025 |
| | X11530 | 4.41E−055 | | | | |
| | bilirubinZZ | 3.02E−018 | | | | |
| | X11381 | 1.09E−007 | | | | |
| X11443 | X11244 | 8.93E−113 | rs16845476 | LRP1B | | 4.65E−006 |
| | dehydroisoandrosteronesulfateDHEAS | 4.10E−106 | | | | |
| | epiandrosteronesulfate | 6.06E−093 | | | | |
| | X11450 | 2.17E−037 | | | | |
| | X12844 | 3.73E−010 | | | | |
| X11444 | X11470 | 5.28E−088 | rs12466713 | BIRC6 | | 3.30E−006 |
| | X12844 | 1.35E−048 | | | | |
| | cortisone | 3.28E−007 | | | | |
| | taurolithocholate3sulfate | 3.91E−007 | | | | |
| X11445 | X11440 | 1.13E−045 | rs13358334 | UGT3A1 | UDP glycosyltransferase 3 family, polypeptide A1 | 2.36E−012 |
| | pyroglutamine | 2.38E−009 | | | | |
| X11450 | dehydroisoandrosteronesulfateDHEAS | 1.11E−101 | rs17325782 | NCKAP5 | | 1.75E−006 |
| | X11443 | 2.17E−037 | | | | |
| | epiandrosteronesulfate | 1.61E−011 | | | | |
| X11452 | X12231 | 0 | rs253444 | | | 1.84E−006 |
| | piperine | 1.38E−031 | | | | |
| X11469 | X02269 | 0 | rs4712963 | | | 5.57E−008 |
| X11470 | X11444 | 5.28E−088 | rs879154 | | | 4.09E−007 |
| | cortisol | 1.80E−019 | | | | |
| | X11440 | 5.45E−011 | | | | |
| | X11244 | 4.12E−009 | | | | |
| | @1oleoylglycerophosphocholine | 1.29E−007 | | | | |
| | heme | 3.11E−007 | | | | |
| X11478 | | | rs16946426 | GPC5 | | 4.40E−007 |
| X11483 | | | rs10505816 | | | 5.91E−008 |
| X11485 | X01911 | 8.36E−010 | rs17361212 | | | 5.50E−007 |
| | X12231 | 3.80E−009 | | | | |
| | @1palmitoylglycerophosphocholine | 4.10E−007 | | | | |
| X11491 | | | rs4149056 | SLCO1B1 | solute carrier organic anion | 7.76E−008 |

TABLE 3-continued

| UN-KNOWN | SIGNIF GGM CORR PARTNER | PVAL GGM | BEST ASSOCIATING SNP | LOCUS dbSNP | DESC LOCUS | PVAL SNP |
|---|---|---|---|---|---|---|
| | | | | | transporter family, member 1B1 | |
| X11497 | X11317 | 1.58E−032 | rs17265949 | NOSTRIN | | 1.60E−007 |
| | X14977 | 2.02E−009 | | | | |
| | pelargonate90 | 1.24E−007 | | | | |
| X11521 | | | rs6082408 | | | 5.39E−007 |
| X11529 | | | rs4149056 | SLCO1B1 | solute carrier organic anion transporter family, member 1B1 | 3.28E−081 |
| X11530 | bilirubinZZ | 8.97E−085 | rs6742078 | UGT1A1; UGT1A10; UGT1A3; UGT1A4; UGT1A5; UGT1A6; UGT1A7; UGT1A8; UGT1A9 | UDP glucuronosyltransferase 1 family, polypeptide A | 2.12E−038 |
| | X11442 | 4.41E−055 | | | | |
| | X11441 | 1.18E−008 | | | | |
| X11537 | X11540 | 0 | rs1529294 | CNTNAP5 | | 8.72E−006 |
| | glucose | 1.47E−007 | | | | |
| X11538 | octadecanedioate | 7.60E−059 | rs4149056 | SLCO1B1 | solute carrier organic anion transporter family, member 1B1 | 1.35E−037 |
| | X12253 | 4.01E−012 | | | | |
| | X12063 | 1.19E−011 | | | | |
| | X11438 | 6.88E−007 | | | | |
| X11540 | X11537 | 0 | rs10798980 | | | 1.64E−006 |
| | choline | 2.06E−013 | | | | |
| | X14977 | 5.54E−007 | | | | |
| X11546 | | | rs17700286 | | | 2.58E−006 |
| X11550 | pelargonate90 | 9.78E−035 | rs894282 | | | 3.69E−006 |
| | heme | 3.89E−011 | | | | |
| | bilirubinEZorZE | 6.24E−007 | | | | |
| X11552 | oleamide | 8.95E−012 | rs12512174 | SORBS2 | | 1.06E−006 |
| X11568 | | | rs10449290 | PLD5 | | 3.55E−006 |
| X11593 | X01911 | 2.98E−038 | rs4680 | COMT | catechol-O-methyltransferase | 1.13E−048 |
| | ascorbateVitaminC | 6.59E−020 | | | | |
| | threonate | 6.92E−020 | | | | |
| | X12206 | 1.98E−011 | | | | |
| | @15anhydroglucitol15AG | 1.26E−007 | | | | |
| | Cglycosyltryptophan | 7.68E−007 | | | | |
| X11786 | pipecolate | 1.55E−021 | rs7251736 | LRRC68 | | 3.11E−007 |
| | Nacetylornithine | 8.11E−010 | | | | |
| X11787 | Nacetylornithine | 8.24E−035 | rs6710438 | ALMS1 (NAT8) | Alstrom syndrome 1 | 2.95E−037 |
| | X11247 | 7.05E−007 | | | | |
| | uridine | 7.06E−007 | | | | |
| X11792 | | | rs4253252 | KLKB1 | kallikrein B, plasma (Fletcher factor) 1 | 1.60E−010 |
| X11793 | bilirubinEE | 8.57E−108 | rs887829 | UGT1A1; UGT1A10; UGT1A3; UGT1A4; UGT1A5; UGT1A6; UGT1A7; UGT1A8; UGT1A9 | UDP glucuronosyltransferase 1 family, polypeptide A | 2.59E−026 |
| X11795 | linolenatealphaorgamma183n3or6 | 4.74E−008 | rs9506615 | | | 1.39E−006 |
| X11799 | stachydrine | 1.14E−017 | rs358231 | GBA3 | glucosidase, beta, acid 3 (cytosolic) | 2.87E−017 |
| | scylloinositol | 8.55E−011 | | | | |
| | X14086 | 6.47E−007 | | | | |
| X11805 | X14208 | 6.14E−062 | rs10475541 | | | 1.57E−006 |
| | X14478 | 3.95E−055 | | | | |
| | X06307 | 4.70E−042 | | | | |
| | aspartylphenylalanine | 1.39E−021 | | | | |
| | DSGEGDFXAEGGGVR | 9.79E−021 | | | | |
| | X14205 | 1.49E−017 | | | | |
| | X14450 | 2.95E−011 | | | | |
| X11809 | bilirubinEE | 2.60E−020 | rs17008568 | | | 8.73E−007 |
| | cholesterol | 1.74E−009 | | | | |
| | X11204 | 2.98E−008 | | | | |
| | stearoylcarnitine | 1.59E−007 | | | | |
| | bilirubinZZ | 1.86E−007 | | | | |
| | glycerophosphorylcholineGPC | 2.51E−007 | | | | |
| | bilirubinEZorZE | 3.37E−007 | | | | |
| X11818 | X12510 | 5.22E−039 | rs196676 | | | 1.31E−007 |
| | linolenatealphaorgamma183n3or6 | 3.01E−007 | | | | |
| | linoleate182n6 | 3.83E−007 | | | | |
| X11820 | | | rs2298423 | | | 3.18E−007 |
| X11826 | | | rs7111693 | | | 4.51E−006 |
| X11843 | | | rs690526 | WDR72 | | 8.88E−008 |
| X11845 | | | rs10895514 | | | 4.09E−006 |

TABLE 3-continued

| UN-KNOWN | SIGNIF GGM CORR PARTNER | PVAL GGM | BEST ASSOCIATING SNP | LOCUS dbSNP | DESC LOCUS | PVAL SNP |
|---|---|---|---|---|---|---|
| X11847 | X11849 | 0 | rs2432626 | SNX29 | | 1.43E-006 |
| | X01911 | 2.41E-047 | | | | |
| | X12231 | 1.91E-013 | | | | |
| | X11438 | 1.66E-008 | | | | |
| | @4ethylphenylsulfate | 6.53E-007 | | | | |
| X11849 | X11847 | 0 | rs7227515 | THOC1 | | 3.84E-006 |
| | X01911 | 1.09E-038 | | | | |
| | X12231 | 1.91E-008 | | | | |
| | @1stearoylglycerophosphoinositol | 1.03E-007 | | | | |
| X11850 | | | rs2003334 | SLC41A3 | | 3.82E-006 |
| X11852 | | | rs895900 | FREM2 | | 1.70E-006 |
| X11858 | | | rs1849474 | | | 9.87E-008 |
| X11859 | pelargonate90 | 1.12E-067 | rs196703 | | | 5.81E-006 |
| X11876 | | | rs13190556 | | | 1.77E-006 |
| X11880 | X11261 | 3.66E-007 | rs4149056 | SLCO1B1 | solute carrier organic anion transporter family, member 1B1 | 6.73E-007 |
| | eicosapentaenoateEPA205n3 | 4.36E-007 | | | | |
| X12013 | | | rs10493639 | | | 4.28E-006 |
| X12029 | X14588 | 2.05E-026 | rs7555956 | SPATA17 | | 3.31E-006 |
| X12038 | X11317 | 1.49E-028 | rs913112 | | | 9.83E-006 |
| | X12524 | 1.10E-016 | | | | |
| | cholesterol | 3.50E-008 | | | | |
| | X13372 | 6.56E-008 | | | | |
| X12039 | quinate | 3.05E-054 | rs4908527 | | | 1.03E-007 |
| | X05426 | 7.82E-037 | | | | |
| | caffeine | 1.07E-018 | | | | |
| | X12217 | 2.63E-014 | | | | |
| | X14473 | 2.14E-011 | | | | |
| | X09789 | 6.63E-011 | | | | |
| | @3methoxytyrosine | 3.43E-009 | | | | |
| | theophylline | 2.32E-008 | | | | |
| | piperine | 1.01E-007 | | | | |
| X12056 | | | rs1345015 | | | 3.07E-006 |
| X12063 | thromboxaneB2 | 1.08E-015 | rs10242455 | CYP3A5 | | 1.47E-045 |
| | dehydroisoandrosteronesulfateDHEAS | 3.96E-013 | | | | |
| | X11538 | 1.19E-011 | | | | |
| | @7alphahydroxy3oxo4cholestenoate7Hoca | 1.13E-007 | | | | |
| X12092 | | | rs4488133 | PYROXD2 | pyridine nucleotide-disulphide oxidoreductase domain 2 | 2.24E-281 |
| X12093 | | | rs4488133 | PYROXD2 | pyridine nucleotide-disulphide oxidoreductase domain 2 | 1.35E-027 |
| X12094 | X12095 | 0 | rs2596210 | RYR3 | | 3.32E-007 |
| X12095 | X12094 | 0 | rs10928512 | TMEM163 | | 2.00E-006 |
| X12100 | kynurenine | 2.02E-033 | rs6151896 | MSH3 | | 3.68E-007 |
| X12116 | | | rs704381 | PRICKLE2 | | 6.66E-007 |
| X12188 | | | rs10026884 | GABRB1 | | 5.59E-006 |
| X12206 | X11593 | 1.98E-011 | rs13416390 | LRRTM4 | | 6.32E-006 |
| | X01911 | 4.77E-007 | | | | |
| X12212 | | | rs4915559 | CFHR4 | | 7.43E-007 |
| X12216 | | | rs2736003 | | | 2.59E-006 |
| X12217 | catecholsulfate | 5.67E-185 | rs1383950 | CSMD1 | | 4.48E-006 |
| | X12039 | 2.63E-014 | | | | |
| X12230 | | | rs12504564 | TMEM144 | | 1.37E-007 |
| X12231 | X11452 | 0 | rs2741110 | | | 5.06E-006 |
| | X11847 | 1.91E-013 | | | | |
| | X11485 | 3.80E-009 | | | | |
| | X11849 | 1.91E-008 | | | | |
| | @3methyl2oxovalerate | 2.30E-007 | | | | |
| X12236 | | | rs6083461 | ZNF343 | | 9.04E-007 |
| X12244 | X04495 | 5.33E-012 | rs10508017 | ABCC4 | | 2.88E-009 |
| | creatinine | 2.54E-007 | | | | |
| X12253 | X09789 | 9.90E-025 | rs7936703 | KCNQ1 | | 3.80E-006 |
| | X11538 | 4.01E-012 | | | | |
| | betaine | 2.93E-007 | | | | |
| X12261 | | | rs2576810 | PTH2R | | 6.29E-007 |
| X12405 | @3indoxylsulfate | 0 | rs7564502 | LRP1B | | 3.03E-007 |
| | DSGEGDFXAEGGGVR | 2.64E-007 | | | | |
| | @2hydroxypalmitate | 6.66E-007 | | | | |

TABLE 3-continued

| UN-KNOWN | SIGNIF GGM CORR PARTNER | PVAL GGM | BEST ASSO-CIATING SNP | LOCUS dbSNP | DESC LOCUS | PVAL SNP |
|---|---|---|---|---|---|---|
| X12407 | | | rs1475525 | DAPK1 | | 8.07E−007 |
| X12428 | | | rs3205166 | DDX58 | | 3.39E−006 |
| X12441 | arachidonate204n6 | 1.52E−116 | rs138832 | BRD1 | | 1.02E−006 |
| | @1arachidonoylglycerophosphocholine | 9.39E−013 | | | | |
| | docosahexaenoateDHA226n3 | 2.74E−009 | | | | |
| | X10810 | 2.26E−007 | | | | |
| | dihomolinolenate203n3orn6 | 6.48E−007 | | | | |
| X12442 | X13069 | 5.73E−026 | rs2279502 | | | 8.86E−008 |
| | @5dodecenoate121n7 | 3.91E−025 | | | | |
| | myristoleate141n5 | 1.04E−016 | | | | |
| | linoleate182n6 | 1.84E−016 | | | | |
| | X13431 | 5.43E−012 | | | | |
| | laurylcarnitine | 1.78E−008 | | | | |
| | dihomolinoleate202n6 | 2.14E−008 | | | | |
| | hypoxanthine | 2.26E−008 | | | | |
| | myristate140 | 7.54E−008 | | | | |
| | @2tetradecenoylcarnitine | 3.61E−007 | | | | |
| X12443 | | | rs13256631 | RGS22 | | 3.53E−007 |
| X12450 | | | rs11760020 | BMP6 | | 5.31E−008 |
| X12456 | | | rs4149056 | SLCO1B1 | solute carrier organic anion transporter family, member 1B1 | 8.41E−017 |
| X12465 | | | rs7723967 | | | 2.24E−006 |
| X12510 | X11818 | 5.22E−039 | rs7598396 | ALMS1 (NAT8?) | Alstrom syndrome 1 | 1.53E−056 |
| | Nacetylornithine | 1.25E−037 | | | | |
| | @10undecenoate111n1 | 6.15E−008 | | | | |
| X12524 | X12038 | 1.10E−016 | rs10497004 | | | 1.66E−006 |
| | X11317 | 1.52E−010 | | | | |
| | palmitate160 | 1.84E−009 | | | | |
| | X13859 | 1.08E−007 | | | | |
| X12544 | | | rs798598 | | | 6.05E−006 |
| X12556 | threonine | 4.59E−019 | rs1550642 | | | 6.63E−007 |
| | X04495 | 4.26E−008 | | | | |
| X12627 | eicosenoate201n9or11 | 2.05E−007 | rs3798720 | ELOVL2 | | 1.86E−007 |
| X12644 | @1arachidonoylglycerophospho-ethanolamine | 1.11E−154 | rs6505683 | | | 4.49E−007 |
| | @1docosahexaenoylglycerophosphocholine | 2.13E−036 | | | | |
| | docosahexaenoateDHA226n3 | 3.89E−020 | | | | |
| | @1linoleoylglycerophosphoethanolamine | 1.29E−007 | | | | |
| X12645 | | | rs168190 | | | 4.09E−007 |
| X12680 | | | rs7477871 | PARD3 | | 3.14E−006 |
| X12696 | @15anhydroglucitol15AG | 7.82E−174 | rs1936074 | | | 6.65E−007 |
| X12704 | | | rs13129177 | | | 7.26E−007 |
| X12711 | | | rs11242244 | | | 3.60E−007 |
| X12717 | | | rs6695534 | SSBP3 | | 1.64E−006 |
| X12719 | | | rs11670870 | | | 1.15E−006 |
| X12726 | | | rs1015150 | TFEB | | 5.66E−006 |
| X12728 | | | rs11831314 | | | 2.25E−006 |
| X12729 | | | rs13246970 | SDK1 | | 8.53E−008 |
| X12734 | | | rs12725733 | | | 1.48E−006 |
| X12740 | | | rs2301920 | CARD11 | | 1.90E−006 |
| X12749 | X11423 | 2.88E−150 | rs6507247 | | | 5.04E−007 |
| X12771 | | | rs802441 | | | 6.40E−007 |
| X12776 | X13619 | 4.14E−007 | rs6429539 | | | 3.89E−006 |
| X12786 | X04357 | 9.02E−096 | rs17406291 | | | 7.00E−007 |
| | lactate | 1.06E−008 | | | | |
| | aspartate | 4.79E−007 | | | | |
| X12798 | @dehydrocarnitine | 1.95E−062 | rs316020 | SLC22A2 | solute carrier family 22 (organic cation transporter), member 2 | 1.73E−072 |
| | X11381 | 5.21E−010 | | | | |
| | X06307 | 2.74E−007 | | | | |
| X12816 | | | rs13275783 | | | 1.70E−006 |
| X12830 | | | rs12517012 | | | 2.23E−007 |
| X12844 | X11444 | 1.35E−048 | rs465226 | SLC35F1 | | 1.15E−006 |
| | X11440 | 2.73E−010 | | | | |
| | X11443 | 3.73E−010 | | | | |
| | thromboxaneB2 | 1.48E−009 | | | | |
| | dehydroisoandrosteronesulfateDHEAS | 2.01E−008 | | | | |
| | epiandrosteronesulfate | 1.72E−007 | | | | |
| X12847 | | | rs9517904 | CLYBL | | 4.54E−006 |
| X12850 | | | rs11019976 | FAT3 | | 3.68E−008 |
| X12851 | | | rs11029926 | | | 4.43E−007 |
| X12855 | | | rs3820881 | SPATS2L | | 6.14E−006 |

TABLE 3-continued

| UN-KNOWN | SIGNIF GGM CORR PARTNER | PVAL GGM | BEST ASSO-CIATING SNP | LOCUS dbSNP | DESC LOCUS | PVAL SNP |
|---|---|---|---|---|---|---|
| X12990 | docosahexaenoateDHA226n3 | 4.56E−037 | rs2524299 | FADS2 | | 9.74E−008 |
| | eicosapentaenoateEPA205n3 | 1.41E−023 | | | | |
| | @3carboxy4methyl5propyl-2furanpropanoateCMPF | 2.60E−021 | | | | |
| | dihomolinolenate203n3orn6 | 6.15E−020 | | | | |
| | @1arachidonoylglycerophosphocholine | 1.21E−017 | | | | |
| | X10810 | 5.78E−008 | | | | |
| | adrenate224n6 | 9.70E−008 | | | | |
| | docosapentaenoaten3DPA225n3 | 1.21E−007 | | | | |
| | arachidonate204n6 | 1.98E−007 | | | | |
| X13069 | X12442 | 5.73E−026 | rs1958375 | | | 1.26E−006 |
| X13183 | linoleamide182n6 | 3.36E−044 | rs10935295 | | | 3.21E−007 |
| | @2stearoylglycerophosphocholine | 5.89E−008 | | | | |
| | oleamide | 1.74E−007 | | | | |
| X13215 | | | rs11880261 | AKT2 | | 4.20E−008 |
| X13372 | X05491 | 2.81E−008 | rs1995973 | | | 2.00E−006 |
| | X12038 | 6.56E−008 | | | | |
| | bilirubinEZorZE | 9.56E−008 | | | | |
| | @4ethylphenylsulfate | 6.70E−007 | | | | |
| X13429 | | | rs4149056 | SLCO1B1 | solute carrier organic anion transporter family, member 1B1 | 4.86E−022 |
| X13431 | @10undecenoate111n1 | 1.82E−014 | rs2286963 | ACADL | acyl-CoA dehydrogenase, long chain | 2.68E−033 |
| | @2methylbutyroylcarnitine | 6.68E−013 | | | | |
| | X12442 | 5.43E−012 | | | | |
| | @1palmitoleoylglycerophosphocholine | 2.75E−007 | | | | |
| X13435 | X11421 | 9.93E−056 | rs2745454 | C6orf146 | | 8.22E−007 |
| | acetylcarnitine | 2.03E−017 | | | | |
| | @2tetradecenoylcarnitine | 3.89E−012 | | | | |
| | hexanoylcarnitine | 1.11E−010 | | | | |
| | X04495 | 5.76E−008 | | | | |
| X13477 | Nacetylornithine | 6.71E−034 | rs6753344 | ALMS1 (NAT8?) | Alstrom syndrome 1 | 1.04E−007 |
| X13496 | erythrose | 3.87E−008 | rs1867237 | GOSR2 | | 1.26E−006 |
| X13548 | X13549 | 1.51E−094 | rs6882355 | EFNA5 | | 3.55E−006 |
| X13549 | X13548 | 1.51E−094 | rs17122693 | ATL1 | | 2.68E−006 |
| X13553 | | | rs17135372 | MCC | | 4.14E−006 |
| X13619 | X09706 | 6.34E−112 | rs1478903 | | | 6.59E−006 |
| | urea | 3.71E−036 | | | | |
| | asparagine | 2.10E−011 | | | | |
| | X10506 | 5.15E−009 | | | | |
| | X02973 | 2.09E−008 | | | | |
| | X12776 | 4.14E−007 | | | | |
| X13640 | | | rs7716072 | FSTL4 | | 2.29E−006 |
| X13671 | | | rs4684510 | | | 6.78E−007 |
| X13741 | | | rs3014887 | | | 1.66E−006 |
| X13859 | X14625 | 3.30E−032 | rs17817518 | RYR3 | | 4.14E−006 |
| | X12524 | 1.08E−007 | | | | |
| X14056 | X14057 | 9.43E−141 | rs2224768 | | | 1.64E−006 |
| | bilirubinEE | 7.85E−017 | | | | |
| X14057 | X14056 | 9.43E−141 | rs6659821 | | | 3.61E−006 |
| X14086 | stachydrine | 4.76E−058 | rs4351 | ACE | angiotensin I converting enzyme (peptidyl-dipeptidase A) 1 | 4.02E−009 |
| | X14304 | 1.54E−027 | | | | |
| | X14189 | 1.21E−025 | | | | |
| | X14208 | 1.83E−014 | | | | |
| | X14205 | 1.34E−012 | | | | |
| | @15anhydroglucitol15AG | 3.03E−008 | | | | |
| | DSGEGDFXAEGGGVR | 5.77E−007 | | | | |
| | X11799 | 6.47E−007 | | | | |
| X14189 | X14304 | 1.45E−204 | rs4343 | ACE | angiotensin I converting enzyme (peptidyl-dipeptidase A) 1 | 1.48E−016 |
| | X14086 | 1.21E−025 | | | | |
| | aspartylphenylalanine | 3.74E−016 | | | | |
| | DSGEGDFXAEGGGVR | 3.05E−008 | | | | |
| X14205 | X14478 | 4.22E−087 | rs4351 | ACE | angiotensin I converting enzyme (peptidyl-dipeptidase A) 1 | 3.97E−014 |
| | DSGEGDFXAEGGGVR | 1.89E−035 | | | | |
| | cysteineglutathionedisulfide | 9.59E−033 | | | | |
| | X14208 | 2.25E−024 | | | | |
| | X11805 | 1.49E−017 | | | | |
| | X06307 | 2.24E−016 | | | | |
| | X14086 | 1.34E−012 | | | | |
| | X14450 | 1.73E−012 | | | | |
| | ADSGEGDFXAEGGGVR | 3.29E−009 | | | | |
| | aspartate | 6.52E−009 | | | | |
| | phenylalanine | 3.18E−007 | | | | |

TABLE 3-continued

| UN-KNOWN | SIGNIF GGM CORR PARTNER | PVAL GGM | BEST ASSOCIATING SNP | LOCUS dbSNP | DESC LOCUS | PVAL SNP |
|---|---|---|---|---|---|---|
| | glutamate | 4.19E-007 | | | | |
| | ADpSGEGDFXAEGGGVR | 6.26E-007 | | | | |
| X14208 | X14478 | 4.67E-153 | rs4351 | ACE | angiotensin I converting enzyme (peptidyl-dipeptidase A) 1 | 4.58E-015 |
| | X11805 | 6.14E-062 | | | | |
| | X14205 | 2.25E-024 | | | | |
| | X14086 | 1.83E-014 | | | | |
| | lysine | 5.68E-011 | | | | |
| X14304 | X14189 | 1.45E-204 | rs4325 | ACE | angiotensin I converting enzyme (peptidyl-dipeptidase A) 1 | 2.68E-012 |
| | X14086 | 1.54E-027 | | | | |
| X14374 | X14473 | 2.57E-098 | rs1374273 | | | 4.19E-007 |
| | theobromine | 8.53E-045 | | | | |
| | hippurate | 6.51E-017 | | | | |
| | quinate | 3.66E-007 | | | | |
| X14450 | aspartylphenylalanine | 5.43E-067 | rs644045 | | | 1.02E-005 |
| | X14478 | 4.67E-014 | | | | |
| | X14205 | 1.73E-012 | | | | |
| | X11805 | 2.95E-011 | | | | |
| X14473 | X14374 | 2.57E-098 | rs7828363 | | | 1.86E-007 |
| | quinate | 2.66E-017 | | | | |
| | X12039 | 2.14E-011 | | | | |
| | theophylline | 1.13E-008 | | | | |
| | bradykinindesarg9 | 5.15E-007 | | | | |
| X14478 | X14208 | 4.67E-153 | rs7239408 | | | 4.67E-006 |
| | X14205 | 4.22E-087 | | | | |
| | X11805 | 3.95E-055 | | | | |
| | X14450 | 4.67E-014 | | | | |
| | cysteineglutathionedisulfide | 5.67E-014 | | | | |
| | aspartylphenylalanine | 3.51E-010 | | | | |
| X14486 | | | rs10079220 | | | 1.79E-007 |
| X14541 | | | rs1026975 | ANK2 | ankyrin 2, neuronal | 9.57E-007 |
| X14588 | X12029 | 2.05E-026 | rs6853408 | CCDC158 | | 7.24E-007 |
| | pipecolate | 2.88E-013 | | | | |
| | histidine | 1.29E-007 | | | | |
| X14625 | X13859 | 3.30E-032 | rs6558292 | OPLAH | | 4.18E-009 |
| | @5oxoproline | 8.59E-028 | | | | |
| | glucose | 3.49E-018 | | | | |
| X14626 | | | rs4149081 | SLCO1B1 | solute carrier organic anion transporter family, member 1B1 | 2.08E-013 |
| X14632 | | | rs10484128 | | | 7.48E-007 |
| X14658 | | | rs11265831 | | | 1.22E-006 |
| X14662 | | | rs12093439 | | | 1.83E-007 |
| X14663 | | | rs7914737 | | | 2.42E-007 |
| X14745 | | | rs6560714 | | | 5.15E-007 |
| X14977 | X11497 | 2.02E-009 | rs16834673 | | | 1.16E-006 |
| | X06246 | 1.46E-008 | | | | |
| | X11540 | 5.54E-007 | | | | |

The invention claimed is:

1. A method of determining the structure of an unknown metabolite when the accurate mass of the metabolite is known, comprising:
    (a) measuring amounts of known and unknown metabolites in subjects;
    (b) associating an unknown metabolite with a specific gene using a genome wide association study;
    (c) determining a protein associated with the specific gene and analyzing information for the protein;
    (d) associating the unknown metabolite with concentrations and/or ratios of other metabolites in the subjects using a partial correlation network;
    (e) obtaining chemical structural data for the unknown metabolite using a mass spectrometer; and
    (f) correlating the results obtained from steps (a) through (e) to determine the structure of the unknown metabolite.

2. The method of claim 1, wherein the specific gene comprises a genetic polymorphism.

3. The method of claim 1, further comprising reviewing the structure and/or characteristics of other metabolites associated with the specific gene from the genome wide association study and/or identifying the biochemical pathway with which at least a portion of the other metabolites associated with the specific gene are involved prior to performing step (f).

4. The method of claim 1, further comprising reviewing the structure and/or characteristics of the other metabolites associated with the unknown metabolite using the partial correlation network and/or identifying the biochemical pathway with which at least a portion of the other metabolites are involved prior to performing step (f).

5. The method of claim 1, wherein the mass spectrometric data of the unknown metabolite comprises mass, molecular formula, or fragmentation spectra.

6. The method of claim 1, wherein the information concerning the protein known to be associated with the gene includes function of the protein.

7. The method of claim 1, wherein the protein performs a metabolic function.

8. The method of claim 1, wherein the protein is an enzyme.

9. The method of claim 8, wherein the substrate of the enzyme is identified.

10. The method of claim 9, wherein the information includes the biochemical pathway for the substrate.

11. The method of claim 9, wherein the information includes alternative biochemical pathways for the substrate.

12. The method of claim 8, wherein an alternative substrate of the enzyme is determined.

13. The method of claim 12, wherein the information includes the biochemical pathway for the substrate.

14. The method of claim 1, wherein the protein is a transporter.

15. The method of claim 3, wherein reviewing the structure and/or characteristics of the other metabolites associated with the specific gene from the genome wide association study and/or metabolites associated using the partial correlation network includes reviewing mass, class of compound, retention time, isotope patterns, fragments, and functionality of the other metabolites.

16. The method of claim 1, wherein the association between the protein and the specific gene is the protein being encoded by the gene.

17. A method of determining the structure of an unknown metabolite when the accurate mass of the metabolite is known, comprising:
(a) measuring amounts of known and unknown metabolites in subjects;
(b) associating an unknown metabolite with a specific gene from a genome wide association study;
(c) determining a protein associated with the specific gene and analyzing information for the protein;
(d) reviewing the structure and/or characteristics of other metabolites associated with the specific gene from the genome wide association study;
and/or identifying the biochemical pathway with which at least a portion of the other metabolites associated with the specific gene are involved;
(e) obtaining chemical structural data for the unknown metabolite using a mass spectrometer; and
(f) correlating results obtained from steps (a) through (e) to determine the structure of the unknown metabolite.

18. A method of determining the structure of an unknown metabolite when the accurate mass of the metabolite is known, comprising:
(a) measuring amounts of known and unknown metabolites in subjects;
(b) associating an unknown metabolite with concentrations and/or ratios of other metabolites in the subjects using a partial correlation network;
(c) reviewing the structure and/or characteristics of the other metabolites associated with the unknown metabolite; and/or identifying the biochemical pathway with which at least a portion of the other metabolites associated with the unknown metabolite are involved;
(d) obtaining chemical structural data for the unknown metabolite using a mass spectrometer; and
(e) correlating the results obtained from steps (a) through (d) to determine the structure of the unknown metabolite.

19. The method of claim 18, further comprising associating the unknown metabolite with a specific gene from a genome wide association study and determining a protein associated with the specific gene and analyzing information for the protein.

* * * * *